(12) United States Patent
Wagner et al.

(10) Patent No.: US 7,247,469 B2
(45) Date of Patent: Jul. 24, 2007

(54) NON-SPECIFIC BINDING RESISTANT PROTEIN ARRAYS AND METHODS FOR MAKING THE SAME

(75) Inventors: Peter Wagner, Belmont, CA (US); Peter Kernen, Foster City, CA (US); Hongbo Lu, Fremont, CA (US); Huu Tran, San Jose, CA (US)

(73) Assignee: Zyomyx, Inc., Hayward, CA (US)

( * ) Notice: Subject to any disclaimer, the term of this patent is extended or adjusted under 35 U.S.C. 154(b) by 0 days.

(21) Appl. No.: 11/137,457

(22) Filed: May 24, 2005

(65) Prior Publication Data

US 2005/0214855 A1 Sep. 29, 2005

Related U.S. Application Data

(63) Continuation of application No. 10/046,442, filed on Oct. 27, 2001, now Pat. No. 6,897,073, which is a continuation-in-part of application No. 09/353,555, filed on Jul. 14, 1999, now Pat. No. 6,329,209, which is a continuation-in-part of application No. 09/115,455, filed on Jul. 14, 1998, now Pat. No. 6,406,921.

(51) Int. Cl.
*C12M 1/34* (2006.01)

(52) U.S. Cl. ............... 435/287.2; 435/6; 435/287.9; 435/810; 435/973; 436/518; 436/524; 436/525; 436/527; 436/809

(58) Field of Classification Search ............ 435/6, 435/287.1, 287.2; 436/518, 524, 525, 809; 422/57

See application file for complete search history.

(56) References Cited

U.S. PATENT DOCUMENTS 5,532,128 A * 7/1996 Eggers et al. .............. 435/6
6,635,311 B1 * 10/2003 Mirkin et al. ............. 427/256

OTHER PUBLICATIONS

Ex parte reexamination request filed against U.S. Patent No. 6,573,369 to Henderson et al. on Nov. 30, 2005.
Non-final Office action, dated Jun. 30, 2006, in the ex parte reexamination of the U.S. Patent No. 6,573,369 to Henderson et al., control No. 90/007,832.

* cited by examiner

*Primary Examiner*—Christopher L. Chin
(74) *Attorney, Agent, or Firm*—Klarquist Sparkman, LLP

(57) ABSTRACT

Arrays of protein-capture agents useful for the simultaneous detection of a plurality of proteins which are the expression products, or fragments thereof, of a cell or population of cells in an organism are provided. A variety of antibody arrays, in particular, are described. Methods of both making and using the arrays of protein-capture agents are also disclosed. The invention arrays are particularly useful for various proteomics applications including assessing patterns of protein expression and modification in cells.

27 Claims, 9 Drawing Sheets

A - A:

NON-SPECIFIC BINDING RESISTANT PROTEIN ARRAYS AND METHODS FOR MAKING THE SAME

CROSS REFERENCE TO RELATED APPLICATIONS

This application is a continuation of U.S. patent application Ser. No. 10/046,442, filed Oct. 27, 2001 now U.S. Pat. No. 6,897,073, which is a continuation-in-part of U.S. patent application Ser. No. 09/353,555 filed Jul. 14, 1999 (now U.S. Pat. No. 6,329,209), which is a continuation-in-part of U.S. patent application Ser. No. 09/115,455 filed Jul. 14, 1998 (now U.S. Pat. No. 6,406,921). The disclosures of these prior filings are hereby incorporated by reference in their entirety for all purposes.

BACKGROUND OF THE INVENTION a) Field of the Invention

The present invention relates generally to arrays of protein-capture agents and methods for the parallel detection and analysis of up to a large number of proteins in a sample. More specifically, the present invention relates to proteomics and the measurement of gene activity at the protein level in cells.

b) Description of Related Art

Although attempts to evaluate gene activity and to decipher biological processes including those of disease processes and drug effects have traditionally focused on genomics, proteomics offers a more direct and promising look at the biological functions of a cell. Proteomics involves the qualitative and quantitative measurement of gene activity by detecting and quantitating expression at the protein level, rather than at the messenger RNA level. Proteomics also involves the study of non-genome encoded events including the post-translational modification of proteins, interactions between proteins, and the location of proteins within the cell. The structure, function, or level of activity of the proteins expressed by a cell are also of interest. Essentially, proteomics involves the study of part or all of the status of the total protein contained within or secreted by a cell.

The study of gene expression at the protein level is important because many of the most important cellular processes are regulated by the protein status of the cell, not by the status of gene expression. Also, the protein content of a cell is highly relevant to drug discovery efforts since most drugs are designed to be active against protein targets.

Measuring the mRNA abundances of a cell provides only an indirect and incomplete assessment of the protein content of a cell. The level of active protein that is produced in a cell is often determined by factors other than the amount of mRNA produced. For instance, both protein maturation and protein degradation are actively controlled in the cell and a protein's activity status can be regulated by post-translational modifications. Studies comparing mRNA transcript abundances to protein abundances have found only a limited correlation (coefficient of about 0.43-0.48) between the two (Anderson and Anderson, *Electrophoresis,* 19:1853-1861, 1998). Furthermore, the extreme lability of RNA in samples due to chemical and enzymatic degradation makes the evaluation of genetic expression at the protein level more practical than at the mRNA level.

Current technologies for the analysis of proteomes are based on a variety of protein separation techniques followed by identification of the separated proteins. The most popular method is based on 2D-gel electrophoresis followed by "in-gel" proteolytic digestion and mass spectroscopy. Alternatively, Edman methods may be used for the sequencing. This 2D-gel technique requires large sample sizes, is time consuming, and is currently limited in its ability to reproducibly resolve a significant fraction of the proteins expressed by a human cell. Techniques involving sonic large-format 2D-gels can produce gels which separate a larger number of proteins than traditional 2D-gel techniques, but reproducibility is still poor and over 95% of the spots cannot be sequenced due to limitations with respect to sensitivity of the available sequencing techniques. The electrophoretic techniques are also plagued by a bias towards proteins of high abundance.

Standard assays for the presence of an analyte in a solution, such as those commonly used for diagnostics, for instance, involve the use of an antibody which has been raised against the targeted antigen. Multianalyte assays known in the art involve the use of multiple antibodies and are directed towards assaying for multiple analytes. However, these multianalyte assays have not been directed towards assaying the total or partial protein content of a cell or cell population. Furthermore, sample sizes required to adapt such standard antibody assay approaches to the analysis of even a fraction of the estimated 100,000 or more different proteins of a human cell and their various modified states are prohibitively large. Automation and/or miniaturization of antibody assays are required if large numbers of proteins are to be assayed simultaneously. Materials, surface coatings, and detection methods used for macroscopic immunoassays and affinity purification are not readily transferable to the formation or fabrication of miniaturized protein arrays.

Miniaturized DNA chip technologies have been developed (for example, see U.S. Pat. Nos. 5,412,087, 5,445,934, and 5,744,305) and are currently being exploited for the screening of gene expression at the mRNA level. These chips can be used to determine which genes are expressed by different types of cells and in response to different conditions. However, DNA biochip technology is not transferable to protein-binding assays such as antibody assays because the chemistries and materials used for DNA biochips are not readily transferable to use with proteins. Nucleic acids such as DNA withstand temperatures up to 100° C., can be dried and re-hydrated without loss of activity, and can be bound physically or chemically directly to organic adhesion layers supported by materials such as glass while maintaining their activity. In contrast, proteins such as antibodies are preferably kept hydrated and at ambient temperatures are sensitive to the physical and chemical properties of the support materials. Therefore, maintaining protein activity at the liquid-solid interface requires entirely different immobilization strategies than those used for nucleic acids. The proper orientation of the antibody or other protein at the interface is desirable to ensure accessibility of their active sites with interacting molecules. With miniaturization of the chip and decreased feature sizes, the ratio of accessible to non-accessible and the ratio of active to inactive antibodies or proteins become increasingly relevant and important.

Thus, there is a need for the ability to assay in parallel a multitude of proteins expressed by a cell or a population of cells in an organism, including up to the total set of proteins expressed by the cell or cells.

SUMMARY OF THE INVENTION

The present invention is directed to arrays of protein-capture agents and methods of use thereof that satisfy the need to assay in parallel a multitude of proteins expressed by a cell or population of cells in an organism, including up to the total protein content of a cell.

In one embodiment, the present invention provides an array of protein-capture agents comprising: a substrate; at least one organic thinfilm covering some or all of the surface of the substrate; and a plurality of patches arranged in discrete, known regions on the portions of the substrate surface covered by organic thinfilm, wherein (i) each patch comprises protein-capture agents immobilized on the organic thinfilm, where the protein-capture agents of a given patch are capable of binding a particular expression product, or a fragment thereof, of a cell or population of cells in an organism; and (ii) the array comprises a plurality of different protein-capture agents, each of which is capable of binding a different expression product, or fragment thereof, of the cell or population of cells in the organism.

In a second embodiment, the invention provides an array of bound proteins which comprises both the array of protein-capture agents of the invention and a plurality of different proteins which are expression products, or fragments thereof, of a cell or population of cells in an organism, where each of the different proteins is bound to a protein-capture agent on a separate patch of the array.

Methods of using the arrays of protein-capture agents of the invention are also provided. In one embodiment of the invention, a method of assaying in parallel for a plurality of different proteins in a sample which are expression products, or fragments thereof, of a cell or a population of cells in an organism, is provided which comprises first delivering the sample to the array of protein-capture agents of the invention under conditions suitable for protein binding, wherein each of the proteins being assayed is a binding partner of the protein-capture agent of at least one patch on the array. The final step comprises detecting, either directly or indirectly, for the presence or amount of protein bound to each patch of the array. This method optionally further comprises the step of further characterizing the proteins bound to at least one patch of the array.

In another embodiment of the invention, a method for determining the protein expression pattern of a cell or a population of cells in an organism is provided which comprises first delivering a sample containing the expression products, or fragments thereof, of the cell or population of cells to the array of protein-capture agents of the invention under conditions suitable for protein binding. The final step comprises detecting, either directly or indirectly, for the presence or amount of protein bound to each patch of the array. In an alternative embodiment, a similar method for comparing the protein expression patterns of two cells or populations of cells is also provided.

In still another embodiment of the invention, an alternative method of assaying in parallel for a plurality of different proteins in a sample which are expression products, or fragments thereof, of a cell or a population of cells in an organism is provided. The method of this embodiment comprises first contacting the sample with an array of spatially distinct patches of different protein-capture agents under conditions suitable for protein binding, wherein each of the proteins being assayed is a binding partner of the protein-capture agent of at least one patch on the array. The last step of the method involves detecting, either directly or indirectly, for the presence or amount of protein bound to each patch of the array.

In a still further embodiment, a method of producing an array of protein-capture agents is provided which comprises the following steps: selecting protein-capture agents from a library of protein-capture agents, wherein the protein-capture agents are selected by their binding affinity to the proteins from a cellular extract or body fluid; producing a plurality of purified samples of the selected protein-capture agents; and immobilizing the protein-capture agent of each different purified sample onto an organic thinfilm on a separate patch on the substrate surface to form a plurality of patches of protein-capture agents on discrete, known regions of the surface of a substrate.

In an alternative embodiment, the invention provides a method for producing an array of protein-capture agents which comprises a first step of selecting protein-capture agents from a library of protein-capture agents, wherein the protein-capture agents are selected by their binding affinity to proteins which are the expression products, or fragments thereof, of a cDNA expression library. The second step of the method comprises producing a plurality of purified samples of the protein-capture agents selected in the first step. The third step comprises immobilizing the protein-capture agent of each different purified sample onto an organic thinfilm on a separate patch on the substrate surface to form a plurality of patches of protein-capture agents on discrete, known regions of the surface of a substrate.

In another aspect, the invention provides for array devices comprising a substrate having a surface; and, one or more protein immobilization regions on said surface, said protein immobilization regions each comprising; an ordered hydrophobic monolayer formed of alkyl chains having proximal ends which are chemisorbed or physisorbed to said surface within said immobilization regions, and opposite hydrophobic distal ends; a hydrophilic monolayer attached to said ordered hydrophobic monolayer, said hydrophilic monolayer comprising a set of first hydrophilic chains, each first hydrophilic chain having a proximal end by which said first hydrophilic chain is linked to an alkyl chain distal end, and an opposite hydrophilic distal end having a functional group for covalently attaching a protein capture agent thereto; one or more of said protein capture agents attached to a first subset of said set of first hydrophilic chains within said immobilization regions through a residue formed by reacting said protein capture agents with said functional groups of said first subset of said first hydrophilic chains; and, one or more second hydrophilic chains each being attached to a second subset of said set of said first hydrophilic chains through said functional group or residue thereof, wherein said second subset of first hydrophilic chains and said first subset of first hydrophilic chains are mutually exclusive of each other; wherein said first hydrophilic chains and said second hydrophilic chains are effective to resist non-specific protein binding. In preferred embodiments, the device has said second hydrophilic chains being polyethylene glycol chains and/or said first hydrophilic chains being oligoethylene glycol chains and/or at least two of said protein immobilization regions being adjacent each other and/or at least two of said protein immobilization regions are separated from each other by one or more border regions.

In another aspect, the invention provides for a method for making an array device comprising the steps of: providing a substrate having a surface; and one or more protein immobilization regions on said surface, said protein immobilization regions each comprising; an ordered hydrophobic monolayer formed of alkyl chains having proximal ends which are chemisorbed or physisorbed to said surface within said immobilization regions, and opposite hydrophobic distal ends; a hydrophilic monolayer attached to said ordered hydrophobic monolayer, said hydrophilic monolayer comprising a set of first hydrophilic chains, each first hydrophilic chain having a proximal end by which said first hydrophilic chain is linked to an alkyl chain distal end, and an opposite hydrophilic distal end; one or more functional groups each for covalently attaching a protein capture agent thereto and each covalently attached to one or more of said hydrophilic distal ends of said first hydrophilic chains; reacting one or more of said protein capture agents to one or more of said functional groups attached to a first subset of said set of first hydrophilic chains within said immobilization regions to attach said one or more protein capture agents through a residue formed by said reaction of said protein capture agents with said functional groups of said first subset of said first hydrophilic chains; and, reacting one or more second hydrophilic chains with a second subset of said set of first hydrophilic chains so that one or more of said second hydrophilic chains attach through one or more residues of one or more of said second subset of said first hydrophilic chains. In preferred embodiments, the method has at least one of said second hydrophilic chains being polyethylene glycol and/or at least one of said first hydrophilic chains being oligoethylene glycol.

A method for making an array device comprising the steps of: providing a substrate having a surface; and one or more protein immobilization regions on said surface, said protein immobilization regions each comprising; an ordered hydrophobic monolayer formed from a set of alkyl chains having proximal ends which are chemisorbed or physisorbed to said surface within said immobilization regions, and opposite hydrophobic distal ends; one or more functional groups for covalently attaching said protein captures agent thereto, each functional group being attached to said hydrophobic distal ends of a subset of said set of alkyl chains; reacting one or more of said protein capture agents to one or more of said functional groups attached to a first subset of said set of alkyl chains within said immobilization regions to attach said one or more protein capture agents through a residue formed by said reaction of said protein capture agents with said functional groups of said first subset of said alkyl chains; and, reacting one or more hydrophilic chains with a second subset of said set of alkyl chains so that one or more of said second hydrophilic chains attach through one or more residues of one or more of said second subset of said set of alkyl chains, wherein said first subset of said set of alkyl chains and said second subset of said set of alkyl chains are mutually exclusive. In preferred embodiments, at least one of said hydrophilic chains is polyethylene glycol, and/or at least one of said first hydrophilic chains is oligoethylene glycol.

DETAILED DESCRIPTION OF THE INVENTION

Figure 1:
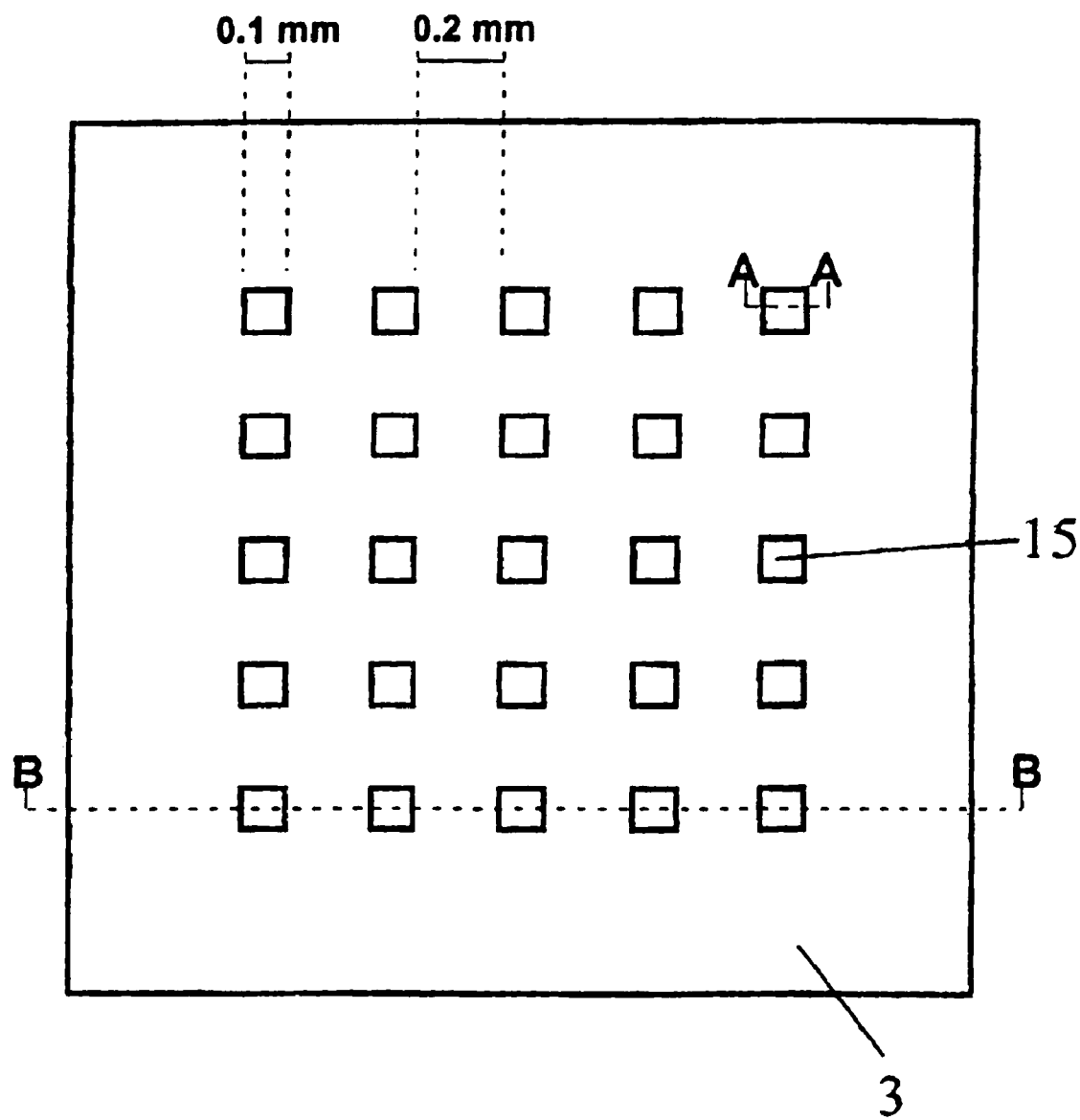
FIG. 1 shows the top view of an array of patches reactive towards protein-capture agents.

A variety of arrays of protein-capture agents and methods useful for multianalyte analyses and analyses of protein expression and modification in cells are provided by the present invention.

(a) Definitions.

The term "protein-capture agent" means a molecule or a multi-molecular complex which can bind a protein to itself. Protein-capture agents preferably bind their binding partners in a substantially specific manner. Protein-capture agents with a dissociation constant ($K_D$) of less than about $10^{-6}$ are preferred. The protein-capture agent will most typically be a biomolecule such as a protein or a polynucleotide. The biomolecule may optionally be a naturally occurring, recombinant, or synthetic biomolecule. Antibodies or antibody fragments are highly suitable as protein-capture agents. Antigens may also serve as protein-capture agents, since they are capable of binding antibodies. A receptor which binds a protein ligand is another example of a possible protein-capture agent. For instance, protein-capture agents are understood not to be limited to agents which only interact with their binding partners through noncovalent interactions. Protein-capture agents may also optionally become covalently attached to proteins which they bind. For instance, the protein-capture agent may be photocrosslinked to its binding partner following binding.

The term "binding partner" means a protein which is bound by a particular protein-capture agent, preferably in a substantially specific manner. In some cases, the protein-capture agent may be a cellular or extracellular protein and the binding partner may be the entity normally bound in vivo. In other embodiments, however, the binding partner may be the protein or peptide on which the protein-capture agent was selected (through in vitro or in vivo selection) or raised (as in the case of antibodies). A binding partner may be shared by more than one protein-capture agent. For instance, a binding partner which is bound by a variety of polyclonal antibodies may bear a number of different epitopes. One protein-capture agent may also bind to a multitude of binding partners, for instance, if the binding partners share the same epitope.

A "protein" means a polymer of amino acid residues linked together by peptide bonds. The term, as used herein, refers to proteins, polypeptides, and peptides of any size, structure, or function. Typically, however, a protein will be at least six amino acids long. Preferably, if the protein is a short peptide, it will be at least about 10 amino acid residues long. A protein may be naturally occurring, recombinant, or synthetic, or any combination of these. A protein may also be just a fragment of a naturally occurring protein or peptide. A protein may be a single molecule or may be a multi-molecular complex. The term protein may also apply to amino acid polymers in which one or more amino acid residues is an artificial chemical analogue of a corresponding naturally occurring amino acid. An amino acid polymer in which one or more amino acid residues is an "unnatural"

amino acid, not corresponding to any naturally occurring amino acid, is also encompassed by the use of the term "protein" herein.

A "fragment of a protein" means a protein which is a portion of another protein. For instance, fragments of a proteins may be a polypeptides obtained by digesting full-length protein isolated from cultured cells. A fragment of a protein will typically comprise at least six amino acids. More typically, the fragment will comprise at least ten amino acids. Preferably, the fragment comprises at least about 16 amino acids.

An "expression product" is a biomolecule, such as a protein, which is produced when a gene in an organism is expressed. An expression product may optionally comprise post-translational modifications.

The term "antibody" means an immunoglobulin, whether natural or partially or wholly synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. Derivatives of the IgG class, however, are preferred in the present invention.

The term "antibody fragment" refers to any derivative of an antibody which is less than full-length. Preferably, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Single-chain Fvs (scFvs) are recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility.

"Diabodies" are dimeric scFvs. The components of diabodies typically have shorter peptide linkers than most scFvs and they show a preference for associating as dimers.

An "Fv" fragment consists of one $V_H$ and one $V_L$ domain held together by noncovalent interactions. The term "dsFv" is used herein to refer to an Fv with an engineered intermolecular disulfide bond to stabilize the $V_H$-$V_L$ pair.

A "F(ab')$_2$" fragment is an antibody fragment essentially equivalent to that obtained from immunoglobulins (typically IgG) by digestion with an enzyme pepsin at pH 4.0-4.5. The fragment may be recombinantly produced.

A "Fab'" fragment is an antibody fragment essentially equivalent to that obtained by reduction of the disulfide bridge or bridges joining the two heavy chain pieces in the F(ab')$_2$ fragment. The Fab' fragment may be recombinantly produced.

A "Fab" fragment is an antibody fragment essentially equivalent to that obtained by digestion of immunoglobulins (typically IgG) with the enzyme papain. The Fab fragment may be recombinantly produced. The heavy chain segment of the Fab fragment is the Fd piece.

A "population of cells in an organism" means a collection of more than one cell in a single organism or more than one cell originally derived from a single organism. The cells in the collection are preferably all of the same type. They may all be from the same tissue in an organism, for instance. Most preferably, gene expression in all of the cells in the population is identical or nearly identical.

"Conditions suitable for protein binding" means those conditions (in terms of salt concentration, pH, detergent, protein concentration, temperature, etc.) which allow for binding to occur between an immobilized protein-capture agent and its binding partner in solution. Preferably, the conditions are not so lenient that a significant amount of nonspecific protein binding occurs.

A "body fluid" may be any liquid substance extracted, excreted, or secreted from an organism or tissue of an organism. The body fluid need not necessarily contain cells. Body fluids of relevance to the present invention include, but are not limited to, whole blood, serum, urine, plasma, cerebral spinal fluid, tears, sinovial fluid, and amniotic fluid.

An "array" is an arrangement of entities in a pattern on a substrate. Although the pattern is typically a two-dimensional pattern, the pattern may also be a three-dimensional pattern.

A "patch of protein-capture agents" means a discrete region of immobilized protein-capture agents on the surface of a substrate. The patches may be of any geometric shape or may be irregularly shaped. For instance, the patch may be, but need not necessarily be, square in shape.

"Proteomics" means the study of or the characterization of either the proteome or some fraction of the proteome. The "proteome" is the total collection of the intracellular proteins of a cell or population of cells and the proteins secreted by the cell or population of cells. This characterization most typically includes measurements of the presence, and usually quantity, of the proteins which have been expressed by a cell. The function, structural characteristics (such as post translational modification), and location within the cell of the proteins may also be studied. "Functional proteomics" refers to the study of the functional characteristics, activity level, and structural characteristics of the protein expression products of a cell or population of cells.

The term "substrate" refers to the bulk, underlying, and core material of the arrays of the invention.

The terms "micromachining" and "microfabrication" both refer to any number of techniques which are useful in the generation of microstructures (structures with feature sizes of sub-millimeter scale). Such technologies include, but are not limited to, laser ablation, electrodeposition, physical and chemical vapor deposition, photolithography, and wet chemical and dry etching. Related technologies such as injection molding and LIGA (X-ray lithography, electrodeposition, and molding) are also included. Most of these techniques were originally developed for use in semiconductors, microelectronics, and Micro-ElectroMechanical Systems (MEMS) but are applicable to the present invention as well.

The term "coating" means a layer that is either naturally or synthetically formed on or applied to the surface of the substrate. For instance, exposure of a substrate, such as silicon, to air results in oxidation of the exposed surface. In the case of a substrate made of silicon, a silicon oxide coating is formed on the surface upon exposure to air. In other instances, the coating is not derived from the substrate and may be placed upon the surface via mechanical, physical, electrical, or chemical means. An example of this type of coating would be a metal coating that is applied to a silicon or polymer substrate or a silicon nitride coating that is applied to a silicon substrate. Although a coating may be of any thickness, typically the coating has a thickness smaller than that of the substrate.

An "interlayer" is an additional coating or layer that is positioned between the first coating and the substrate. Multiple interlayers may optionally be used together. The primary purpose of a typical interlayer is to aid adhesion between the first coating and the substrate. One such example is the use of a titanium or chromium interlayer to help adhere a gold coating to a silicon or glass surface. However, other possible functions of an interlayer are also anticipated. For instance, some interlayers may perform a role in the detection system of the array (such as a semiconductor or metal layer between a nonconductive substrate and a nonconductive coating).

An "organic thinfilm" is a thin layer of organic molecules which has been applied to a substrate or to a coating on a substrate if present. Typically, an organic thinfilm is less than about 20 nm thick. Optionally, an organic thinfilm may be less than about 10 nm thick. An organic thinfilm may be disordered or ordered. For instance, an organic thinfilm can be amorphous (such as a chemisorbed or spin-coated polymer) or highly organized (such as a Langmuir-Blodgett film or self-assembled monolayer). An organic thinfilm may be heterogeneous or homogeneous. Organic thinfilms which are monolayers are preferred. A lipid bilayer or monolayer is a preferred organic thinfilm. Optionally, the organic thinfilm may comprise a combination of more than one form of organic thinfilm. For instance, an organic thinfilm may comprise a lipid bilayer on top of a self-assembled monolayer. A hydrogel may also compose an organic thinfilm. The organic thinfilm will typically have functionalities exposed on its surface which serve to enhance the surface conditions of a substrate or the coating on a substrate in any of a number of ways. For instance, exposed functionalities of the organic thinfilm are typically useful in the binding or covalent immobilization of the protein-capture agents to the patches of the array. Alternatively, the organic thinfilm may bear functional groups (such as polyethylene glycol (PEG)) which reduce the non-specific binding of molecules to the surface. Other exposed functionalities serve to tehter the thinfilm to the surface of the substrate or the coating. Particular functionalities of the organic thinfilm may also be designed to enable certain detection techniques to be used with the surface. Alternatively, the organic thinfilm may serve the purpose of preventing inactivation of a protein-capture agent or the protein to be bound by a protein-capture agent from occurring upon contact with the surface of a substrate or a coating on the surface of a substrate.

A "monolayer" is a single-molecule thick organic thinfilm. A monolayer may be disordered or ordered. A monolayer may optionally be a polymeric compound, such as a polynonionic polymer, a polyionic polymer, or a block-copolymer. For instance, the monolayer may be composed of a poly(amino acid) such as polylysine. A monolayer which is a self-assembled monolayer, however, is most preferred. One face of the self-assembled monolayer is typically composed of chemical functionalities on the termini of the organic molecules that are chemisorbed or physisorbed onto the surface of the substrate or, if present, the coating on the substrate if present. Examples of suitable functionalities of monolayers include the positively charged amino groups of poly-L-lysine for use on negatively charged surfaces and thiols for use on gold surfaces. Typically, the other face of the self-assembled monolayer is exposed and may bear any number of chemical functionalities (end groups). Preferably, the molecules of the self-assembled monolayer are highly ordered.

A "self-assembled monolayer" is a monolayer which is created by the spontaneous assembly of molecules. The self-assembled monolayer may be ordered, disordered, or exhibit short- to long-range order.

An "affinity tag" is a functional moiety capable of directly or indirectly immobilizing a protein-capture agent onto an exposed functionality of the organic thinfilm. Preferably, the affinity tag enables the site-specific immobilization and thus enhances orientation of the protein-capture agent onto the organic thinfilm. In some cases, the affinity tag may be a simple chemical functional group. Other possibilities include amino acids, poly(amino acid) tags, or full-length proteins. Still other possibilities include carbohydrates and nucleic acids. For instance, the affinity tag may be a polynucleotide which hybridizes to another polynucleotide serving as a functional group on the organic thinfilm or another polynucleotide serving as an adaptor. The affinity tag may also be a synthetic chemical moiety. If the organic thinfilm of each of the patches comprises a lipid bilayer or monolayer, then a membrane anchor is a suitable affinity tag. The affinity tag may be covalently or noncovalently attached to the protein-capture agent. For instance, if the affinity tag is covalently attached to the protein-capture agent it may be attached via chemical conjugation or as a fusion protein. The affinity tag may also be attached to the protein-capture agent via a cleavable linkage. Alternatively, the affinity tag may not be directly in contact with the protein-capture agent. The affinity tag may instead be separated from the protein-capture agent by an adaptor. The affinity tag may immobilize the protein-capture agent to the organic thinfilm either through noncovalent interactions or through a covalent linkage.

An "adaptor", for purposes of this invention, is any entity that links an affinity tag to the protein-capture agent. The adaptor may be, but need not necessarily be, a discrete molecule that is noncovalently attached to both the affinity tag and the protein-capture agent. The adaptor can instead be covalently attached to the affinity tag or the protein-capture agent or both (via chemical conjugation or as a fusion protein, for instance). Proteins such as full-length proteins, polypeptides, or peptides are typical adaptors. Other possible adaptors include carbohydrates or nucleic acids.

The term "fusion protein" refers to a protein composed of two or more polypeptides that, although typically unjoined in their native state, are joined by their respective amino and carboxyl termini through a peptide linkage to form a single continuous polypeptide. It is understood that the two or more polypeptide components can either be directly joined or indirectly joined through a peptide linker/spacer.

The term "normal physiological condition" means conditions that are typical inside a living organism or a cell. While it is recognized that some organs or organisms provide extreme conditions, the intra-organismal and intra-cellular environment normally varies around pH 7 (i.e., from pH 6.5 to pH 7.5), contains water as the predominant solvent, and exists at a temperature above 0° C. and below 50° C. It will be recognized that the concentration of various salts depends on the organ, organism, cell, or cellular compartment used as a reference.

(b) Arrays of the Invention.

The present invention is directed to arrays of protein-capture agents which can bind a plurality of proteins that are the expression products, or fragments thereof, of a cell or population of cells in an organism and therefore can be used to evaluate gene expression at the protein level. Typically, the arrays comprise micrometer-scale, two-dimensional patterns of patches of protein-capture agents immobilized on an organic thinfilm coating on the surface of the substrate.

In one embodiment of the invention, the array of protein-capture agents comprises a substrate, at least one organic thinfilm covering some or all of the surface of the substrate, and a plurality of patches arranged in discrete, known regions on the portions of the substrate surface covered by organic thinfilm, wherein (i) each patch comprises protein-capture agents immobilized on the organic thinfilm, wherein said protein-capture agents of a given patch are capable of binding a particular expression product, or a fragment thereof, of a cell or population of cells in an organism, and (ii) the array comprises a plurality of different protein-capture agents, each of which is capable of binding a different expression product, or fragment thereof, of the cell or population of cells.

The protein-capture agents are preferably covalently immobilized on the patches of the array, either directly or indirectly.

In most cases, the array will comprise at least about ten patches. In a preferred embodiment, the array comprises at least about 50 patches. In a particularly preferred embodiment the array comprises at least about 100 patches. In alternative preferred embodiments, the array of protein-capture agents may comprise more than $10^3$, $10^4$ or $10^5$ patches.

The area of surface of the substrate-covered by each of the patches is preferably no more than about 0.25 mm$^2$. Preferably, the area of the substrate surface covered by each of the patches is between about 1 µm$^2$ and about 10,000 µm$^2$. In a particularly preferred embodiment, each patch covers an area of the substrate surface from about 100 µm$^2$ to about 2,500 µm$^2$. In an alternative embodiment, a patch on the array may cover an area of the substrate surface as small as about 2,500 nm$^2$, although patches of such small size are generally not necessary for the use of the array.

The patches of the array may be of any geometric shape. For instance, the patches may be rectangular or circular. The patches of the array may also be irregularly shaped. The patches are optionally elevated from the median plan of the underlying substrate.

The distance separating the patches of the array can vary. Preferably, the patches of the array are separated from neighboring patches by about 1 µm to about 500 µm. Typically, the distance separating the patches is roughly proportional to the diameter or side length of the patches on the array if the patches have dimensions greater than about 10 µm. If the patch size is smaller, then the distance separating the patches will typically be larger than the dimensions of the patch.

In a preferred embodiment of the array, the patches of the array are all contained within an area of about 1 cm$^2$ or less on the surface of the substrate. In one preferred embodiment of the array, therefore, the array comprises 100 or more patches within a total area of about 1 cm$^2$ or less on the surface of the substrate. Alternatively, a particularly preferred array comprises $10^3$ or more patches within a total area of about 1 cm$^2$ or less. A preferred array may even optionally comprise $10^4$ or $10^5$ or more patches within an area of about 1 cm$^2$ or less on the surface of the substrate. In other embodiments of the invention, all of the patches of the array are contained within an area of about 1 mm$^2$ or less on the surface of the substrate.

In some versions of the array, the diameter of each of the patches is proportional to the distance separating the patches. Therefore, the area of each patch may be from about 100 nm$^2$ to about 40,000 µm$^2$. Each patch preferably has an area from about 1 µm$^2$ to about 10,000 µm$^2$.

Typically, only one type of protein-capture agent is present on a single patch of the array. If more than one type of protein-capture agent is present on a single patch, all of the protein-capture agents of that patch must share a common binding partner. For instance, a patch may comprise a variety of polyclonal antibodies to the same antigen (although potentially, the antibodies may bind different epitopes on that same antigen).

The arrays of the invention can have any number of a plurality of different protein-capture agents. Typically the array comprises at least about ten different protein-capture agents. Preferably, the array comprises at least about 50 different protein-capture agents. More preferably, the array comprises at least about 100 different protein-capture agents. Alternative preferred arrays comprise more than about $10^3$ different protein-capture agents or more than about $10^4$ different protein-capture agents. The array may even optionally comprise more than about $10^5$ different protein-capture agents.

The number of different protein-capture agents on the array will vary depending on the application desired. For instance, if the array is to be used as a diagnostic tool in evaluating the status of a tumor or other diseased tissue in a patient, an array comprising less than about 100 different protein-capture agents may suffice since the necessary binding partners of the protein-capture agent on the array are limited to only those proteins whose expression is known to be indicative of the disease condition. However, if the array is to be used to measure a significant portion of the total protein content of a cell, then the array preferably comprises at least about 10,000 different protein-capture agents. Alternatively, a more limited proteomics study, such as a study of the abundances of various human transcription factors, for instance, might only require an array of about 100 different protein-capture agents.

In one embodiment of the array, each of the patches of the array comprises a different protein-capture agent. For instance, an array comprising about 100 patches could comprise about 100 different protein-capture agents. Likewise, an array of about 10,000 patches could comprise about 10,000 different protein-capture agents. In an alternative embodiment, however, each different protein-capture agent is immobilized on more than one separate patch on the array. For instance, each different protein-capture agent may optionally be present on two to six different patches. An array of the invention, therefore, may comprise about three-thousand protein-capture agent patches, but only comprise about one thousand different protein-capture agents since each different protein-capture agent is present on three different patches.

Typically, the number of different proteins which can be bound by the plurality of different protein-capture agents on the array will be at least about ten. However, it is preferred that the plurality of different protein-capture agents on the array is capable of binding a higher number of different proteins, such as at least about 50 or at least about 100. In still further preferred embodiments, the plurality of different proteins on the array is capable of binding at least about $10^3$ proteins. For some applications, such as those where it is desirable to assay the entire protein content of a cell, or a significant fraction thereof, an array where the plurality of protein-capture agents is capable of binding at least about $10^4$ different proteins or even at least about $10^5$ different proteins is most preferred.

In one embodiment of the invention, the binding partners of the plurality of protein-capture agents on the array are proteins which are all expression products, or fragments thereof, of a cell or population of cells of a single organism. The expression products may be proteins, including peptides, of any size or function. They may be intracellular proteins or extracellular proteins. The expression products may be from a one-celled or multicellular organism. The organism may be a plant or an animal. In a preferred embodiment of the invention, the binding partners are human expression products, or fragments thereof.

In one embodiment of the invention, the binding partners of the protein-capture agents of the array may be a randomly chosen subset of all the proteins, including peptides, which are expressed by a cell or population of cells in a given organism or a subset of all the fragments of those proteins. Thus, the binding partners of the protein-capture agents of the array optionally represent a wide distribution of different proteins from a single organism.

The binding partners of some or all of the protein-capture agents on the array need not necessarily be known. The binding partner of a protein-capture agent of the array may be a protein or peptide of unknown function. For instance, the different protein-capture agents of the array may together bind a wide range of cellular proteins from a single cell type, many of which are of unknown identity and/or function.

In another embodiment of the present invention, the binding partners of the protein-capture agents on the array are related proteins. The different proteins bound by the protein-capture agents may optionally be members of the same protein family. The different binding partners of the protein-capture agents of the array may be either functionally related or just suspected of being functionally related. The different proteins bound by the protein-capture agents of the array may also be proteins which share a similarity in structure or sequence or are simply suspected of sharing a similarity in structure or sequence. For instance, the binding partners of the protein-capture agents on the array may optionally all be growth factor receptors, hormone receptors, neurotransmitter receptors, catecholamine receptors, amino acid derivative receptors, cytokine receptors, extracellular matrix receptors, antibodies, lectins, cytokines, serpins, proteases, kinases, phosphatases, ras-like GTPases, hydrolases, steroid hormone receptors, transcription factors, heat-shock transcription factors. DNA-binding proteins, zinc-finger proteins, leucine-zipper proteins, homeodomain proteins, intracellular signal transduction modulators and effectors, apoptosis-related factors, DNA synthesis factors, DNA repair factors, DNA recombination factors, cell-surface antigens, hepatitis C virus (HCV) proteases or HIV proteases.

In an alternative embodiment of the invention, the proteins which are the binding partners of the protein-capture agents of the array may be fragments of the expression products of a cell or population of cells in an organism.

A protein-capture agent on the array can be any molecule or complex of molecules which has the ability to bind a protein and immobilize it to the site of the protein-capture agent on the array. Preferably, the protein-capture agent binds its binding partner in a substantially specific manner. Hence, the protein-capture agent may optionally be a protein whose natural function in a cell is to specifically bind another protein, such as an antibody or a receptor. Alternatively, the protein-capture agent may instead be a partially or wholly synthetic or recombinant protein which specifically binds a protein. Alternatively, the protein-capture agent may be a protein which has been selected in vitro from a mutagenized, randomized, or completely random and synthetic library by its binding affinity to a specific protein or peptide target. The selection method used may optionally have been a display method such as ribosome display or phage display (see below). Alternatively, the protein-capture agent obtained via in vitro selection may be a DNA or RNA aptamer which specifically bonds a protein target (for example: Potyrailo et al., *Anul. Chem.*, 70:3419-25, 1998; Cohen, et al., *Proc. Natl. Acad. Sci. USA*, 95:14272-7, 1998; Fukuda, et al., *Nucleic Acids Symp. Ser.*, (37):237-8, 1997). Alternatively, the in vitro selected protein-capture agent may be a polypeptide (Roberts and Szostak, *Proc. Natl. Acad. Sci. USA*, 94:12297-302, 1997). In an alternative embodiment, the protein-capture agent may be a small molecule which has been selected from a combinatorial chemistry library or is isolated from an organism.

In a preferred embodiment of the array, however, the protein-capture agents are proteins. In a particularly preferred embodiment, the protein-capture agents are antibodies or antibody fragments. Although antibody moieties are exemplified herein, it is understood that the present arrays and methods may be advantageously employed with other protein-capture agents.

The antibodies or antibody fragments of the array may optionally be single-chain Fvs, Fab fragments, Fab' fragments, F(ab')$_2$ fragments, FV fragments, dsFvs diabodies, Fd fragments, full-length, antigen-specific polyclonal antibodies, or full-length monoclonal antibodies. In a preferred embodiment, the protein-capture agents of the array are monoclonal antibodies, Fab fragments or single-chain Fvs.

The antobodies or antibody fragments may be monoclonal antibodies, even commercially available antibodies, against known, well-characterized proteins. Alternatively, the antibody fragments have been derived by selection from a library using the phage display method. If the antibody fragments are derived individually by selection based on binding affinity to known proteins, then, the binding partners of the antibody fragments are known. In an alternative embodiment of the invention, the antibody fragments have been derived by a phage display method comprising selection based on binding affinity to the (typically, immobilized) proteins of a cellular extract or a body fluid. In this embodiment, some or many of the antibody fragments of the array would bind proteins of unknown identity and/or function.

Upon using the array of protein-capture agents to bind a plurality of expression products, or fragments thereof, an array of bound proteins is created. Thus, another embodiment of the invention provides an array of bound proteins which comprises (a) a protein-capture agent array of the invention and (b) a plurality of different proteins which are expression products, or fragments thereof, of a cell or a population of cells in an organism, wherein each of the different proteins is bound to a protein-capture agent on a separate patch of the array. Preferably, each of the different proteins is non-covalently bound to a protein-capture agent.

(c) Substrates, Coatings, and Organic Thinfilms.

The substrate of the array may be either organic or inorganic, biological or non-biological, or any combination of these materials. In one embodiment, the substrate is transparent or translucent. The portion of the surface of the substrate on which the patches reside is preferably flat and firm or semi-firm. However, the array of the present invention need not necessarily be flat or entirely two-dimensional. Significant topological features may be present on the surface of the substrate surrounding the patches, between the patches or beneath the patches. For instance, walls or other barriers may separate the patches of the array.

Numerous materials are suitable for use as a substrate in the array embodiment of the invention. For instance, the substrate of the invention array can comprise a material selected from a group consisting of silicon, silica, quartz, glass, controlled pore glass, carbon, alumina, titania, tantalum oxide, germanium, silicon nitride, zeolites, and gallium arsenide. Many metals such as gold, platinum, aluminum, copper, titanium, and their alloys are also options for substrates of the array. In addition, many ceramics and polymers may also be used as substrates. Polymers which may be used as substrates include, but are not limited to, the following: polystyrene; poly(tetra)fltioroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyalkenesulfone (PAS); polypropylethylene; polyethylene; polyhydroxyethylmethacrylate (HEMA); polydimethylsiloxane; polyacrylamide; polyimide; and block-copolymers. Preferred substrates for the array include silicon, silica, glass, and polymers. The substrate on which the patches reside may also be a combination of any of the aforementioned substrate materials.

An array of the present invention may optionally further comprise a coating between the substrate and the organic thinfilm of its patches. This coating may either be formed on the substrate or applied to the substrate. The substrate can be modified with a coating by using thin-film technology based, for instance, on physical vapor deposition (PVD), plasma-enhanced chemical vapor deposition (PECVD), or thermal processing. Alternatively, plasma exposure can be used to directly activate or alter the substrate and create a coating. For instance, plasma etch procedures can be used to oxidize a polymeric surface (for example, polystyrene or polyethylene to expose polar functionalities such as hydroxyls, carboxylic acids, alclehydes and the like) which then acts as a coating.

The coating is optionally a metal film. Possible metal films include aluminum, chromium, titanium, tantalum, nickel, stainless steel, zinc, lead, iron, copper, magnesium, manganese, cadmium, tungsten, cobalt, and alloys or oxides thereof. In a preferred embodiment, the metal film is a noble metal film. Noble metals that may be used for a coating include, but are not limited to, gold, platinum, silver, and copper. In an especially preferred embodiment, the coating comprises gold or a gold alloy. Electron-beam evaporation may be used to provide a thin coating of gold on the surface of the substrate. In a preferred embodiment, the metal film is from about 50 nm to about 500 nm in thickness. In an alternative embodiment, the metal film is from about 1 nm to about 1 μm in thickness.

In alternative embodiments, the coating comprises a composition selected from the group consisting of silicon, silicon oxide, titania, tantalum oxide, silicon nitride, silicon hydride, indium tin oxide, magnesium oxide, alumina, glass, hydroxylated surfaces, and polymers.

In one embodiment of the invention array, the surface of the coating is atomically flat. In this embodiment, the mean roughness of the surface of the coating is less than about 5 angstroms for areas of at least 25 μm$^2$. In a preferred embodiment, the mean roughness of the surface of the coating is less than about 3 angstroms for areas of at least 25 μm$^2$. The ultraflat coating can optionally be a template-stripped surface as described in Hegner et al., *Surface Science,* 993, 291:39-46 and Wagner et al., *Longmuir,* 1995, 11:3867-3875, both of which are incorporated herein by reference.

It is contemplated that the coatings of many arrays will require the addition of at least one adhesion layer between said coating and the substrate. Typically, the adhesion layer will be at least 6 angstroms thick and may be much thicker. For instance, a layer of titanium or chromium may be desirable between a silicon wafer and a gold coating. In an alternative embodiment, an epoxy glue such as Epo-tek 377®, Epo-tek 301-2®, (Epoxy Technology Inc., Billerica, Mass.) may be preferred to aid adherence of the coating to the substrate. Determinations as to what material should be used for the adhesion layer would be obvious to one skilled in the art once materials are chosen for both the substrate and coating. In other embodiments, additional adhesion mediators or interlayers may be necessary to improve the optical properties of the array, for instance, waveguides for detection purposes.

Deposition or formation of the coating (if present) on the substrate is performed prior to the formation of the organic thinfilm thereon. Several different types of coating may be combined on the surface. The coating may cover the whole surface of the substrate or only parts of it. The pattern of the coating may or may not be identical to the pattern of organic thinfilms used to immobilize the protein-capture agents. In one embodiment of the invention, the coating covers the substrate surface only at the site of the patches of protein-capture agents. Techniques useful for the formation of coated patches on the surface of the substrate which are organic thinfilm compatible are well known to those of ordinary skill in the art. For instance, the patches of coatings on the substrate may optionally be fabricated by photolithography, micromolding (PCI Publication WO 96/29629), wet chemical or dry etching, or any combination of these.

The organic thinfilm on which each of the patches of protein-capture agents resides forms a layer either on the substrate itself or on a coating covering tie substrate. The organic thinfilm on which the protein-capture agents of the patches are immobilized is preferably less than about 20 nm thick. In some embodiments of the invention, the organic thinfilm of each of the patches may be less than about 10 nm thick.

A variety of different organic thinfilms are suitable for use in the present invention. Methods for the formation of organic thinfilms include in situ growth from the surface, deposition by physisorption, spin-coating, chemisorption, self-assembly, or plasma-initiated polymerization from gas phase. For instance, a hydrogel composed of a material such as dextran can serve as a suitable organic thinfilm on the patches of the array. In one preferred embodiment of the invention, the organic thinfilm is a lipid bilayer. In another preferred embodiment, the organic thinfilm of each of the patches of the array is a monolayer. A monolayer of polyarginine or polylysine adsorbed on a negatively charged substrate or coating is one option for the organic thinfilm. Another option is a disordered monolayer of tethered polymer chains. In a particularly preferred embodiment, the organic thinfilm is a self-assembled monolayer. The organic thinfilm is most preferably a self-assembled monolayer which comprises molecules of the formula X—R—Y, wherein R is a spacer, X is a functional group that binds R to the surface, and Y is a functional group for binding protein-capture agents onto the monolayer. In an alternative preferred embodiment, the self-assembled monolayer is comprised of molecules of the formula $(X)_aR(Y)_b$ where a and b are, independently, integers greater than or equal to 1 and X, R, and Y are as previously defined. In an alternative preferred embodiment, the organic thinfilm comprises a combination of organic thinfilms such as a combination of a lipid bilayer immobilized on top of a self-assembled monolayer of molecules of the formula X—R—Y. As another example, a monolayer of polylysine can also optionally be combined with a self-assembled monolayer of molecules of the formula X—R—Y (see U.S. Pat. No. 5,629,213).

In all cases, the coating, or the substrate itself if no coating is present, must be compatible with the chemical or physical adsorption of the organic thinfilm on its surface. For instance, if the patches comprise a coating between the substrate and a monolayer of molecules of the formula X—R—Y, then it is understood that the coating must be composed of a material for which a suitable functional group X is available (see below). If no such coating is present, then it is understood that the substrate must be composed of a material for which a suitable functional group X is available.

In a preferred embodiment of the invention, the regions of the substrate surface, or coating surface, which separate the patches of protein-capture agents are free of organic thinfilm. In an alternative embodiment, the organic thinfilm extends beyond the area of the substrate surface, or coating surface if present, covered by the patches of protein-capture agents. For instance, optionally, the entire surface of the array may be covered by an organic thinfilm on which the plurality of spatially distinct patches of protein-capture agents reside. An organic thinfilm which covers the entire surface of the array may be homogenous or may optionally comprise patches of the differing exposed functionalities useful in the immobilization of patches of different protein-capture agents. In still another alternative embodiment, the regions of the substrate surface or coating surface, if a coating is present, between the patches of protein-capture agents are covered by an organic thinfilm, but an organic thinfilm of a different type than that of the patches of protein-capture agents. For instance, the surfaces between the patches of protein-capture agents may be coated with an organic thinfilm characterized by low non-specific binding properties for proteins and other analytes.

A variety of techniques may be used to generate patches of organic thinfilm on the surface of the substrate or on the surface of a coating on the substrate. These techniques are well known to those skilled in the art and will vary depending upon the nature of the organic thinfilm, the substrate, and the coating if present. The techniques will also vary depending on the structure of the underlying substrate and the pattern of any coating present on the substrate. For instance, patches of a coating which is highly reactive with an organic thinfilm may have already been produced on the substrate surface. Arrays of patches of organic thinfilm can optionally be created by microfluidics printing, microstamping (U.S. Pat. Nos. 5,512,131 and 5,731,152), or microcontact printing (μCP) (PCT Publication WO 96/29629). Subsequent immobilization of protein-capture agents to the reactive monolayer patches results in two-dimensional arrays of the agents. Inkjet printer heads provide another option for patterning monolayer X—R—Y molecules, or components thereof, or other organic thinfilm components to nanometer or micrometer scale sites on the surface of the substrate or coating (Lemmo et al., *Anal Chem.*, 1997, 69:543-551; U.S. Pat. Nos. 5,843,767 and 5,837,860). In some cases, commercially available arrayers based on capillary dispensing (for instance, OmniGrid™ from Genemachines, inc, San Carlos, Calif., and High-Throughput Microarrayer from Intelligent Bio-Instruments. Cambridge, Mass.) may also be of use in directing components of organic thinfilms to spatially distinct regions of the array.

Diffusion boundaries between the patches of protein-capture agents immobilized on organic thinfilms such as self-assembled monolayers may be integrated as topographic patterns (physical barriers) or surface functionalities with orthogonal wetting behavior (chemical barriers). For instance, walls of substrate material or photoresist may be used to separate some of the patches from some of the others or all of the patches from each other. Alternatively, non-bioreactive organic thinfilms, such as monolayers, with different wettability may be used to separate patches from one another.

In a preferred embodiment of the invention, each of the patches of protein-capture agents comprises a self-assembled monolayer of molecules of the formula X—R—Y, as previously defined, and the patches are separated from each other by surfaces free of the monolayer.

FIG. 1 shows the top view of one example of an array of patches reactive with protein-capture agents. On the array, a number of patches 15 cover the surface of the substrate 3.

Figure 2:
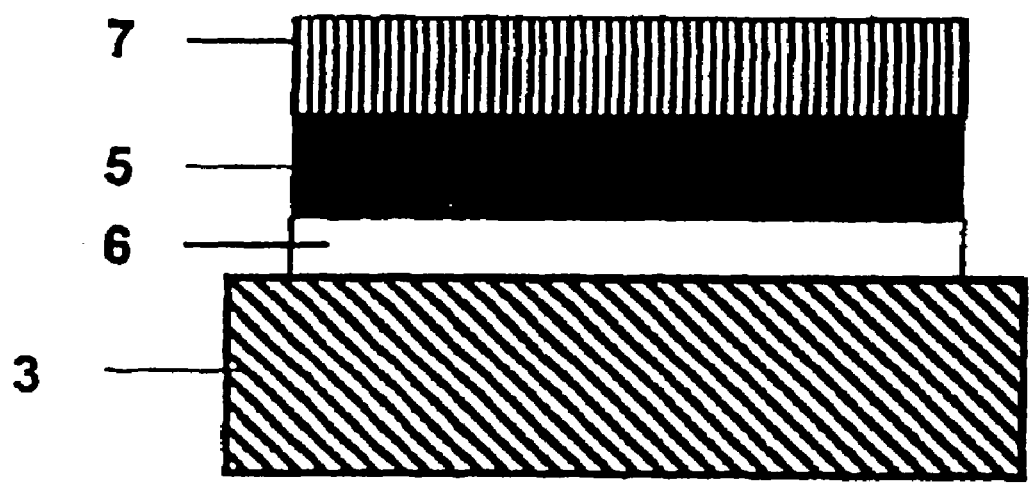
FIG. 2 shows the cross section of an individual patch of the array of FIG. 1.

FIG. 2 shows a detailed cross section of a patch 15 of the array of FIG. 1. This view illustrates the use of a coating 5 on the substrate 3. An adhesion interlayer 6 is also included in the patch. On top of the patch resides a self-assembled monolayer 7.

Figure 3:
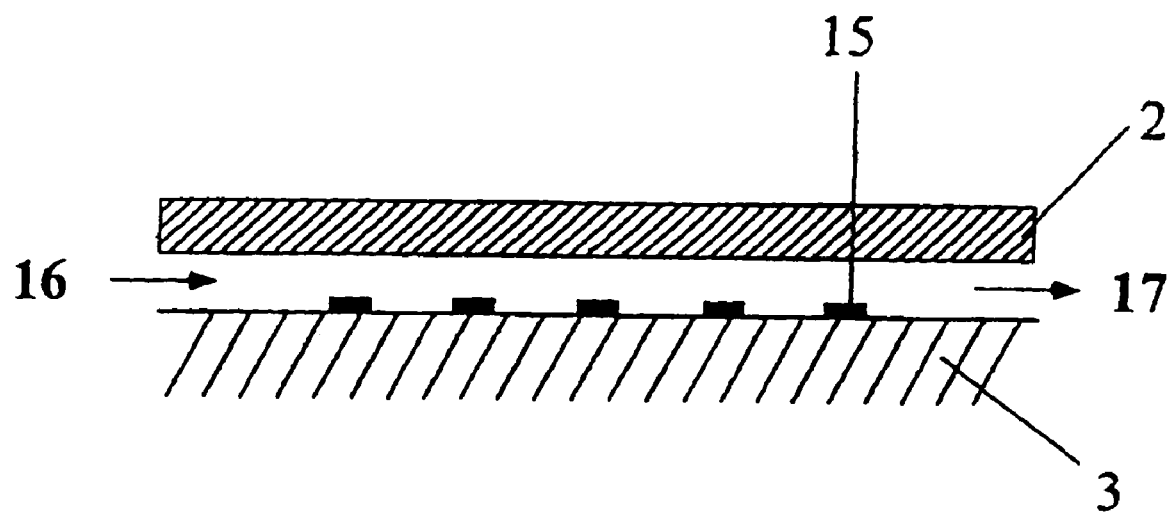
FIG. 3 shows the cross section of a row of monolayer-covered patches of the array of FIG. 1.

FIG. 3 shows a cross section of one row of the patches 15 of the array of FIG. 1. This figure also shows the use of a cover 2 over the array. Use of the cover 2 creates an inlet port 16 and an outlet port 17 for solutions to be passed over the array.

A variety of chemical moieties may function as monolayer molecules of the formula X—R—Y in the array of the present invention. However, three major classes of monolayer formation are preferably used to expose high densities of reactive omega-functionalities on the patches of the array: (i) alkylsiloxane monolayers ("silanes") on hydroxylated and non-hydroxylated surfaces (as taught in, for example, U.S. Pat. No. 5,405,766, PCT Publication WO 96/38726, U.S. Pat. No. 5,412,087, and U.S. Pat. No. 5,688,642); (ii) alkyl-thiol/dialkyidisulfide monolayers on noble metals (preferably Au(111)) (as, for example, described in Allara et al., U.S. Pat. No. 4,690,715; Bamdad et al., U.S. Pat. No. 5,620,850; Wagner et al., *Biophysical Journal*, 1996, 70:2052-2066); and (iii) alkyl monolayer formation on oxide-free passivated silicon (as taught in, for example, Linford et al., *J. Am. Chem. Soc.*, 1995, 117:3145-3155, Wagner et al., *Journal of Structural Biology*, 1997, 119:189-201, U.S. Pat. No. 5,429,708). One of ordinary skill in the art, however, will recognize that many possible moieties may be substituted for X, R, and/or Y, dependent primarily upon the choice of substrate, coating, and affinity tag. Many examples of monolayers are described in Ulman, *An Introduction to Ultrathin Organic Films: From Langmuir-Blodgett to Self Assembly*, Academic press (1991).

In one embodiment, the monolayer comprises molecules of the formula $(X)_aR(Y)_b$ wherein a and b are independently equal to an integer between 1 and about 200. In a preferred embodiment, a and b are, independently, equal to an integer between 1 and about 80. In a more preferred embodiment, a and b are, independently, equal to 1 or 2. In a most preferred embodiment, a and b are both equal to 1 (molecules of the formula X—R—Y).

If the patches of the invention array comprise a self-assembled monolayer of molecules of the formula $(X)_a R (Y)_b$, then R may optionally comprise a linear or branched hydrocarbon chain from about 1 to about 400 carbons long. The hydrocarbon chain may comprise an alkyl, aryl, alkenyl, alkynyl, cycloalkyl, alkaryl, aralkyl group, or any combination thereof. If a and b are both equal to one, then R is typically an alkyl chain from about 3 to about 30 carbons long. In a preferred embodiment, if a and b are both equal to one, then R is an alkyl chain from about 8 to about 22 carbons long and is, optionally, a straight alkane. However, it is also contemplated that in an alternative embodiment, R may readily comprise a linear or branched hydrocarbon chain from about 2 to about 400 carbons long and be interrupted by at least one hetero atom. The interrupting hetero groups can include —O—, —CONH—, —CONHCO—, —NH—, —CSNH—, —CO—, —CS—, —S—, —SO—, —(OCH$_2$CH$_2$)$_n$— (where n=1-20), —(CF$_2$)$_n$— (where n=1-22), and the like. Alternatively, one or more of the hydrogen moieties of R can be substituted with deuterium. In alternative, less preferred, embodiments, R may be more than about 400 carbons long.

X may be chosen as any group which affords chemisorption or physisorption of the monolayer onto the surface of the substrate (or the coating, if present). When the substrate or coating is a metal or metal alloy, X, at least prior to incorporation into the monolayer, can in one embodiment be chosen to be an asymmetrical or symmetrical disulfide, sulfide diselenide, selenide, thiol, isonitrile, selenol, a trivalent phosphorus compound, isothiocyanate, isocyanate, xanthanate, thiocarbamate, a phosphine, an amine, thio acid or a dithio acid. This embodiment is especially preferred when a coating or substrate is used that is a noble metal such as gold, silver, or platinum.

If the substrate of the array is a material such as silicon, silicon oxide, indium tin oxide, magnesium oxide, alumina, quartz, glass, or silica, then the array of one embodiment of the invention comprises an X that, prior to incorporation into said monolayer, is a monohalosilane, dihalosi lane, trihalosilane, trialkoxysilane, dialkoxysilane, or a monoalkoxysilane. Among these silanes, trichlorosilane and trialkoxysilane are particularly preferred.

In a preferred embodiment of the invention, the substrate is selected from the group consisting of silicon, silicon dioxide, indium tin oxide, alumina, glass, and titania; and X, prior to incorporation into said monolayer, is selected from the group consisting of a monohalosilane, dihalosilane, trihalosilane, trichlorosilane, trialkoxysilane, dialkoxysilane, monoalkoxysilane, carboxylic acids, and phosphates.

In another preferred embodiment of the invention, the substrate of the array is silicon and X is an olefin.

In still another preferred embodiment of the invention, the coating (or the substrate if no coating is present) is titania or tantalum oxide and X is a phosphate.

In other embodiments, the surface of the substrate (or coating thereon) is composed of a material such as titanium oxide, tantalum oxide, indium tin oxide, magnesium oxide, or alumina where X is a carboxylic acid or alkylphosphoric acid. Alternatively, if the surface of the substrate (or coating thereon) of the array is copper, then X may optionally be a hydroxamic acid.

If the substrate used in the invention is a polymer, then in many cases a coating on the substrate such as a copper coating will be included in the array. An appropriate functional group X for the coating would then be chosen for use in the array. In an alternative embodiment comprising a polymer substrate, the surface of the polymer may be plasma-modified to expose desirable surface functionalities for monolayer formation. For instance, EP 780423 describes the use of a monolayer molecule that has an alkene X functionality on a plasma exposed surface. Still another possibility for the invention array comprised of a polymer is that the surface of the polymer on which the monolayer is formed is functionalized by copolymerization of appropriately functionalized precursor molecules.

Another possibility is that prior to incorporation into the monolayer, X can be a free-radical-producing moiety. This functional group is especially appropriate when the surface on which the monolayer is formed is a hydrogenated silicon surface. Possible free-radical producing moieties include, but are not limited to, diacylperoxides, peroxides, and azo compounds. Alternatively, unsaturated moieties such as unsubstituted alkenes, alkynes, cyano compounds and isonitrile compounds can be used for X, if the reaction with X is accompanied by ultraviolet, infrared, visible, or microwave radiation.

In alternative embodiments, X, prior to incorporation into the monolayer, may be a hydroxyl, carboxyl, vinyl, sulfonyl, phosphoryl, silicon hydride, or an amino group.

The component, Y, of the monolayer is a functional group responsible for binding a protein-capture agent onto the monolayer. In a preferred embodiment of the invention, the Y group is either highly reactive (activated) towards the protein-capture agent (or its affinity tag) or is easily converted into such an activated form. In a preferred embodiment, the coupling of Y with the protein-capture agent occurs readily under normal physiological conditions not detrimental to the ability of the protein-capture agent to bind its binding partner. The functional group Y may either form a covalent linkage or a noncovalent linkage with the protein-capture agent (or its affinity tag, if present). In a preferred embodiment, the functional group Y forms a covalent linkage with the protein-capture agent or its affinity tag. It is understood that following the attachment of the protein-capture agent (with or without an affinity tag) to Y, the chemical nature of Y may have changed. Upon attachment of the protein-capture agent, Y may even have been removed from the organic thinfilm.

In one embodiment of the array of the present invention, Y is a functional group that is activated in situ. Possibilities for this type of functional group include, but are not limited to, such simple moieties such as a hydroxyl, carboxyl, amino, aldehyde, carbonyl, methyl, methylene, alkene, alkyne, carbonate, aryliodide, or a vinyl group. Appropriate modes of activation would be obvious to one skilled in the art. Alternatively, Y can comprise a functional group that requires photoactivation prior to becoming activated enough to trap the protein-capture agent.

In an especially preferred embodiment of the array of the present invention, Y is a complex and highly reactive functional moiety that is compatible with monolayer formation and needs no in situ activation prior to reaction with the protein-capture agent and/or affinity tag. Such possibilities for Y include, but are not limited to, maleimide, N-hydroxysuccinimide (Wagner et al., *Biophysical Journal*, 1996, 70:2052-2066), nitrilotriacetic acid (U.S. Pat. No. 5,620,850), activated hydroxyl, haloacetyl, bromoacetyl, iodoacetyl, activated carboxyl, hydrazide, epoxy, aziridine, sulfonylchloride, trifluoromethyldiaziridine, pyridyldisulfide, N-acyl-imidazole, imidazolecarbamate, vinylsulfone, succinimidylcarbonate, arylazide, anhydride, diazoacetate, benzophenone, isothiocyanate, isocyanate, imidoester, fluorobenzene, and biotin.

Figure 4:
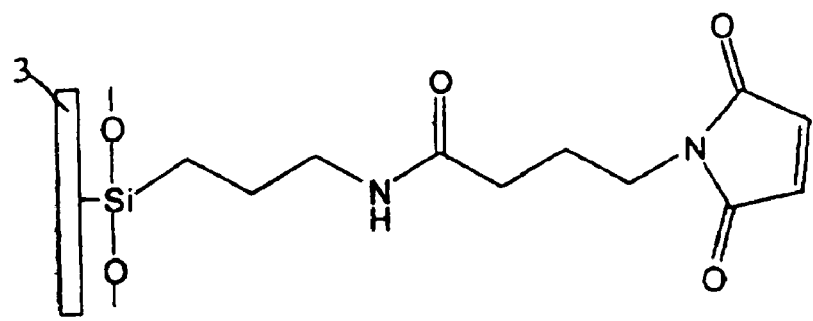
FIG. 4 shows a thiolreactive monolayer on a substrate.

FIG. 4 shows one example of a monolayer on a substrate 3. In this example, substrate 3 comprises glass. The monolayer is thiolreactive because it bears a maleimidyl functional group Y.

Figure 5:
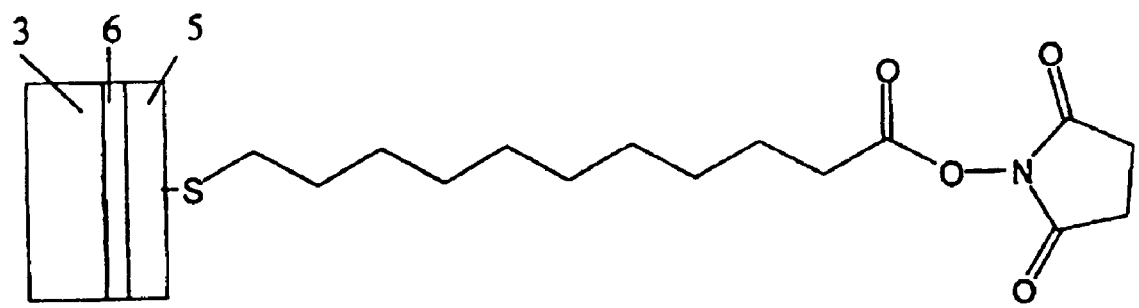
FIG. 5 shows an aminoreactive monolayer on a coated substrate.

FIG. 5 shows another example of a monolayer on a substrate 3 which is silicon. In this case, however, a thinfilm gold coating 5 covers the surface of the substrate 3. Also, in this embodiment, a titanium adhesion interlayer 6 is used to adhere the coating 5 to the substrate 3. This monolayer is aminoreactive because it bears an N-hydroxysuccinimidyl functional group Y.

In an alternative embodiment, the functional group Y of the array is selected from the group of simple functional moieties. Possible Y functional groups include, but are not limited to, —OH, —NH$_2$, —COOH, —COOR, —RSR, —PO$_4^{-3}$, —OSO$_3^{-2}$, —SO$_3^{-}$, —COO$^{-}$, —SOO$^{-}$, —CONR$_2$, —CN, —NR$_2$, and the like.

The monolayer molecules of the present invention can optionally be assembled on the surface in parts. In other words, the monolayer need not necessarily be constructed by chemisorption or physisorption of molecules of the formula X—R—Y to the surface of the substrate (or coating). Instead, in one embodiment, X may be chemisorbed or physisorbed to the surface of the substrate (or coating) alone first. Then, R or even just individual components of R can be attached to X through a suitable chemical reaction. Upon completion of addition of the spacer R to the X moiety already immobilized on the surface, Y can be attached to the ends of the monolayer molecule through a suitable covalent linkage.

Not all self-assembled monolayer molecules on a given patch need be identical to one another. Some patches may comprise mixed monolayers. For instance, the monolayer of an individual patch may optionally comprise at least two different molecules of the formula X—R—Y, as previously described. This second X—R—Y molecule may immobilize the same or a different protein-capture agent having the same binding partner as the first. In addition, some of the monolayer molecules X—R—Y of a patch may have failed to attach any protein-capture agent.

As another alternative embodiment of the invention, a mixed, self-assembled monolayer of an individual patch on the array may comprise both molecules of the formula X—R—Y, as previously described, and molecules of the formula, X—R—V where R is a spacer, X is a functional group that binds R to the surface, and V is a moiety which is biocompatible with proteins and resistant to the non-specific binding of proteins. For example, V may consist of a hydroxyl, saccharide, or oligo/polyethylene glycol moiety (EP Publication 780423).

In still another embodiment of the invention, the array comprises at least one unreactive patch of organic thinfilm on the substrate or coating surface which is devoid of any protein-capture agent. For instance, the unreactive patch may optionally comprise a monolayer of molecules of the formula X—R—V, where R is a spacer, X is a functional group that binds R to the surface, and V is a moiety resistant to the non-specific binding of proteins. The unreactive patch may serve as a control patch or be useful in background binding measurements.

Regardless of the nature of the monolayer molecules, in some arrays it may be desirable to provide crosslinking between molecules of an individual patch's monolayer. In general, crosslinking confers additional stability to the monolayer. Such methods are familiar to those skilled in the art (for instance, see Ulman, *An Introduction to Ultrathin Organic Films: From Langmuir-Blodgelt to Self-Assembly*, Academic Press (1991)).

After completion of formation of the monolayer on the patches, the protein-capture agent may be attached to the monolayer via interaction with the Y-functional group. Y-functional groups which fail to react with any protein-capture agents are preferably quenched prior to use of the array. Quenching may be performed using small molecular weight agents such as glycine with NHS coupling schemes, however a particularly preferred embodiment includes quenching un-reacted Y functional groups with polymeric molecules having non-specific protein binding resistant properties such as polyethylene glycol or PEG. For example, a surface displaying NHS or N-hydroxysuccinamide groups is first reacted with a protein capture agent such as biotin or an antibody or antibody-like molecule, then, the un-reacted NHS Y functional groups are then reacted to amine-PEG to quench the NHS group. An example of a final chip product produced by this method would include a surface, an ordered hydrophobic monolayer formed from hydrocarbon polymer chains attached to the surface, a hydrophilic monolayer formed from hydrophilic polymer chains attached to the hydrophobic monolayer, protein capture agents attached to one or more of the hydrophilic polymer chains of the hydrophilic monolayer, and PEG attached to one or more of any hydrophilic polymer chains lacking a protein capture agent.

Figure 10A:
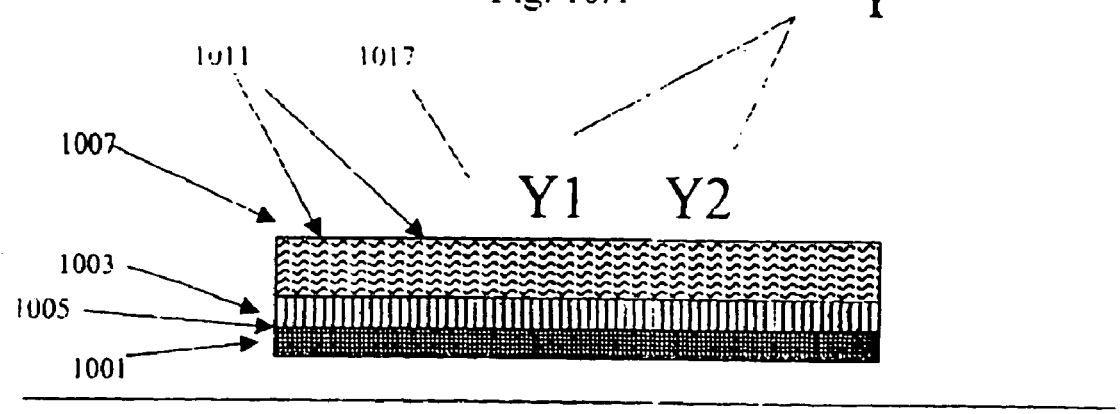
FIGS. 10A-C show several panels where unreacted functional groups are quenched.

FIG. 10A depicts chip (1001) with thinfilm (1003) formed from hydrophobic monolayer (1005) attached to surface (1005) of chip (1001) and hydrophilic monolayer (1007) attached to hydrophobic monolayer (1005). Functional groups (Y) are attached to the end of hydrophilic chains (1011) away from chip surface (1005) to form a functional group bearing surface (1017) outwardly facing away from chip surface (1005).

Figure 10B:
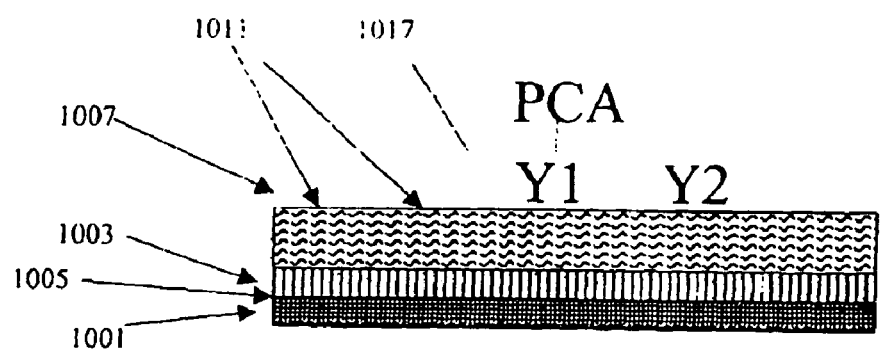

FIG. 10B depicts how a first subset (Y1) of functional groups (Y) are reacted with protein capture agents (PCA) to immobilize such agents to chip (1001).

Figure 10C:
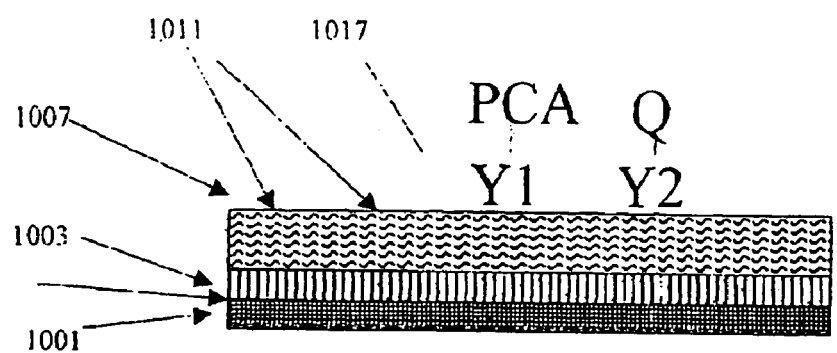

FIG. 10C depicts how a second subset (Y2) of functional groups (Y), which is mutually exclusive of first subset (Y1), is reacted with a quenching agent (Q) to quench unreacted functional groups of second subset (1023).

(d) Affinity Tags and Immobilization of Protein-Capture Agents.

In a preferred embodiment, the protein-immobilizing patches of the array further comprise an affinity tag that enhances immobilization of the protein-capture agent onto the organic thinfilm. The use of an affinity tag on the protein-capture agent of the array typically provides several advantages. An affinity tag can confer enhanced binding or reaction of the protein-capture agent with the functionalities on the organic thinfilm, such as Y if the organic thinfilm is a an X—R—Y monolayer as previously described. This enhancement effect may be either kinetic or thermodynamic. The affinity tag/thinfilm combination used in the patches of the array preferably allows for immobilization of the protein-capture agents in a manner which does not require harsh reaction conditions that are adverse to protein stability or function. In most embodiments, immobilization to the organic thinfilm in aqueous, biological buffers is ideal.

An affinity tag also preferably offers immobilization on the organic thinfilm that is specific to a designated site or location on the protein-capture agent (site-specific immobilization). For this to occur, attachment of the affinity tag to the protein-capture agent must be site-specific. Site-specific immobilization helps ensure that the protein-binding site of the agent, such as the antigen-binding site of the antibody moiety, remains accessible to ligands in solution. Another advantage of immobilization through affinity tags is that it allows for a common immobilization strategy to be used with multiple, different protein-capture agents.

The affinity tag is optionally attached directly, either covalently or noncovalently, to the protein-capture agent. In an alternative embodiment, however, the affinity tag is either covalently or noncovalently attached to an adaptor which is either covalently or noncovalently attached to the protein-capture agent.

In a preferred embodiment, the affinity tag comprises at least one amino acid. The affinity tag may be a polypeptide comprising at least two amino acids which is reactive with the functionalities of the organic thinfilm. Alternatively, the affinity tag may be a single amino acid which is reactive with the organic thinfilm. Examples of possible amino acids which could be reactive with an organic thinfilm include cysteine, lysine, histidine, arginine, tyrosine, aspartic acid, glutamic acid, tryplophan, serine, threonine, and glutamine. A polypeptide or amino acid affinity tag is preferably expressed as a fusion protein with the protein-capture agent when the protein-capture agent is a protein, such as an antibody or antibody fragment. Amino acid affinity tags provide either a single amino acid or a series of amino acids that can interact with the functionality of the organic thinfilm, such as the Y-functional group of the self-assembled monolayer molecules. Amino acid affinity tags can be readily introduced into recombinant proteins to facilitate oriented immobilization by covalent binding to the Y-functional group of a monolayer or to a functional group on an alternative organic thinfilm.

The affinity tag may optionally comprise a poly(amino acid) tag. A poly(amino acid) tag is a polypeptide that comprises from about 2 to about 100 residues of a single amino acid, optionally interrupted by residues of other amino acids. For instance, the affinity tag may comprise a poly-cysteine, polylysine, poly-arginine, or poly-histidine. Amino acid tags are preferably composed of two to twenty residues of a single amino acid, such as, for example, histidines, lysines, arginines, cysteines, glutamines, tyrosines, or any combination of these. According to a preferred embodiment, an amino acid tag of one to twenty amino acids includes at least one to ten cysteines for thioether linkage; or one to ten lysines for amide linkage; or one to ten arginines for coupling to vicinal dicarbonyl groups. One of ordinary skill in the art can readily pair suitable affinity tags with a given functionality on an organic thinfilm.

The position of the amino acid tag can be at an amino-, or carboxy-terminus of the protein-capture agent which is a protein, or anywhere in-between, as long as the protein-binding region of the protein-capture agent, such as the antigen-binding region of an immobilized antibody moiety, remains in a position accessible for protein binding. Where compatible with the protein-capture agent chosen, affinity tags introduced for protein purification are preferentially located at the C-terminus of the recombinant protein to ensure that only full-length proteins are isolated during protein purification. For instance, if intact antibodies are used on the arrays, then the attachment point of the affinity tag on the antibody is preferably located at a C-terminus of the effector (Fc) region of the antibody. If scFvs are used on the arrays, then the attachment point of the affinity tag is also preferably located at the C-terminus of the molecules.

Affinity tags may also contain one or more unnatural amino acids. Unnatural amino acids can be introduced using suppressor tRNAs that recognize stop codons (i.e., amber) (Noren et al., Science, 1989, 244:182-188; Ellman el al., Methods Enzym., 1991, 202:301-336; Cload et al., Chem. Biol., 1996, 3:1033-1038). The tRNAs are chemically amino-acylated to contain chemically altered ("unnatural") amino acids for use with specific coupling chemistries (i.e., ketone modifications, photoreactive groups).

In an alternative embodiment the affinity tag can comprise an intact protein, such as, but not limited to, glutathione S-transferase, an antibody, avidin, or streptavidin.

When the protein-capture agent is a protein and the affinity tag is a protein, such as a poly(amino acid) tag, or a single amino acid, the affinity tag is preferably attached to the protein-capture agent by generating a fusion protein. Alternatively, protein synthesis or protein ligation techniques known to those skilled in the art may be used. For instance, intein-mediated protein ligation may optionally be used to attach the affinity tag to the protein-capture agent (Mathys, et al., Gene 231:1-13, 1999; Evans, et al., Protein Science 7:2256-2264, 1998).

Other protein conjugation and immobilization techniques known in the art may be adapted for the purpose of attaching affinity tags to the protein-capture agent. For instance, in an alternative embodiment of the array, the affinity tag may be an organic bioconjugate which is chemically coupled to the protein-capture agent of interest. Biotin or antigens may be chemically cross linked to the protein. Alternatively, a chemical crosslinker may be used that attaches a simple functional moiety such as a thiol or an amine to the surface of a protein serving as a protein-capture agent on the array.

In an alternative embodiment of the invention, the organic thinfilm of each of the patches comprises, at least in part, a lipid monolayer or bilayer, and the affinity tag comprises a membrane anchor.

Figure 6:
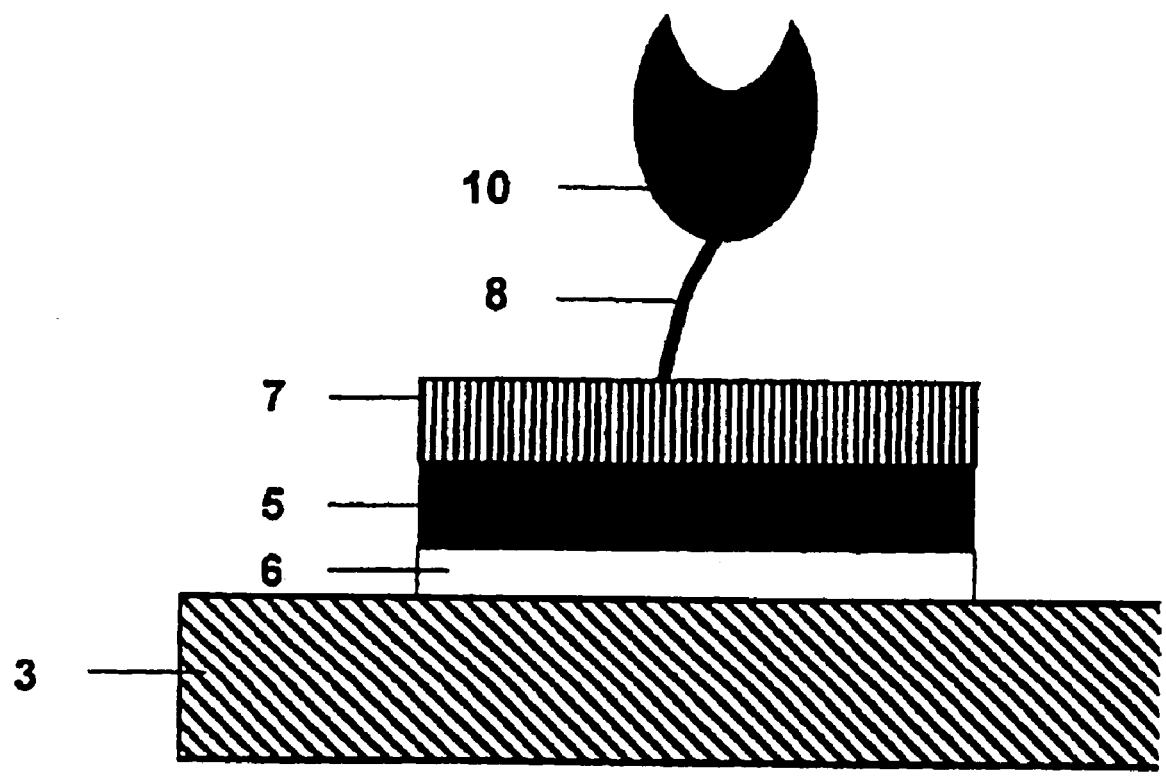
FIG. 6 shows the immobilization of a protein-capture agent on a monolayer-coated substrate via an affinity tag.

FIG. 6 shows a detailed cross section of a patch on one embodiment of the invention array. In this embodiment, a protein-capture agent 10 is immobilized on a monolayer 7 on a substrate 3. An affinity tag 8 connects the protein-capture agent 10 to the monolayer 7. The monolayer 7 is formed on a coating 5 which is separated from the substrate 3 by an interlayer 6.

In an alternative embodiment of the invention, no affinity tag is used to immobilize the protein-capture agents onto the organic thinfilm. An amino acid or other moiety (such as a carbohydrate moiety) inherent to the protein-capture agent itself may instead be used to tether the protein-capture agent to the reactive group of the organic thinfilm. In preferred embodiments, the immobilization is site-specific with respect to the location of the site of immobilization on the protein-capture agent. For instance, the sulfhydryl group on the C-terminal region of the heavy chain portion of a Fab' fragment generated by pepsin digestion of an antibody, followed by selective reduction of the disulfide between monovalent Fab' fragments, may be used as the affinity tag. Alternatively, a carbohydrate moiety on the Fc portion of an intact antibody can be oxidized under mild conditions to an aldehyde group suitable for immobilizing the antibody on a monolayer via reaction with a hydrazide-activated Y group on the monolayer. Examples of immobilization of protein-capture agents without any affinity tag in a site-specific manner can be found in Dammer el al., Biophys J., 70:2437-2441, 1996 and the specific examples, Examples 5-7, below.

Since the protein-capture agents of at least some of the different patches on the array are different from each other, different solutions, each containing a different, preferably, affinity-tagged protein-capture agent, must be delivered to their individual patches. Solutions of protein-capture agents may be transferred to the appropriate patches via arrayers which are well-known in the art and even commercially available. For instance, microcapillary-based dispensing systems may be used. These dispensing systems are preferably automated and computer-aided. A description of and building instructions for an example of a microarrayer comprising an automated capillary system can be found on the internet at http://cmgm.stanford.edu/pbrown/array.html and http://cmgm.stanford.edu/pbrown/mguide/index.html. The use of other microprinting techniques for transferring solutions containing the protein-capture agents to the agent-reactive patches is also possible. Inkjet printer heads may also optionally be used for precise delivery of the protein-capture agents to the agent-reactive patches. Representative, non-limiting disclosures of techniques useful for depositing the protein-capture agents on the patches may be found, for example, in U.S. Pat. No. 5,731,152 (stamping apparatus), U.S. Pat. No. 5,807,522 (capillary dispensing device), U.S. Pat. No. 5,837,860 (inkjet printing technique, Hamilton 2200 robotic pipetting delivery system), and U.S. Pat. No. 5,843,767 (inkjet printing technique, Hamilton 2200 robotic pipetting delivery system), all incorporated by reference herein.

(e) Adaptors.

Another embodiment of the array of the present invention comprises an adaptor that links the affinity tag to the protein-capture agent on the patches of the array. The additional spacing of the protein-capture agent from the surface of the substrate (or coating) that is afforded by the use of an adaptor is particularly advantageous if the protein-capture agent is a protein, since proteins are known to be prone to surface inactivation. The adaptor may optionally afford some additional advantages as well. For instance, the adaptor may help facilitate the attachment of the protein-capture agent to the affinity tag. In another embodiment, the adaptor may help facilitate the use of a particular detection technique with the array. One of ordinary skill in the art will be able to choose an adaptor which is appropriate for a given affinity tag. For instance, if the affinity tag is streptavidin, then the adaptor could be biotin that is chemically conjugated to the protein-capture agent which is to be immobilized.

In one embodiment, the adaptor comprises a protein. In another embodiment, the affinity tag, adaptor, and protein-capture agent together compose a fusion protein. Such a fusion protein may be readily expressed using standard recombinant DNA technology. Adaptors which are proteins are especially useful to increase the solubility of the protein-capture agent of interest and to increase the distance between the surface of the substrate or coating and the protein-capture agent. Use of a protein adaptor can also be very useful in facilitating the preparative steps of protein purification by affinity binding prior to immobilization on the array. Examples of possible adaptor proteins include glutathione-S-transferase (GST), maltose-binding protein, chitin-binding protein, thioredoxin, green-fluorescent protein (GFP). GFP can also be used for quantification of surface binding; In a preferred embodiment, when the protein-capture agent is an antibody moiety comprising the Fc region, the adaptor is a polypeptide, such as protein G, protein A, or recombinant protein A/G (a gene fusion product secreted from a non-pathogenic form of *Bacillus* which contains four Fc binding domains from protein A and two from protein G).

Figure 7:
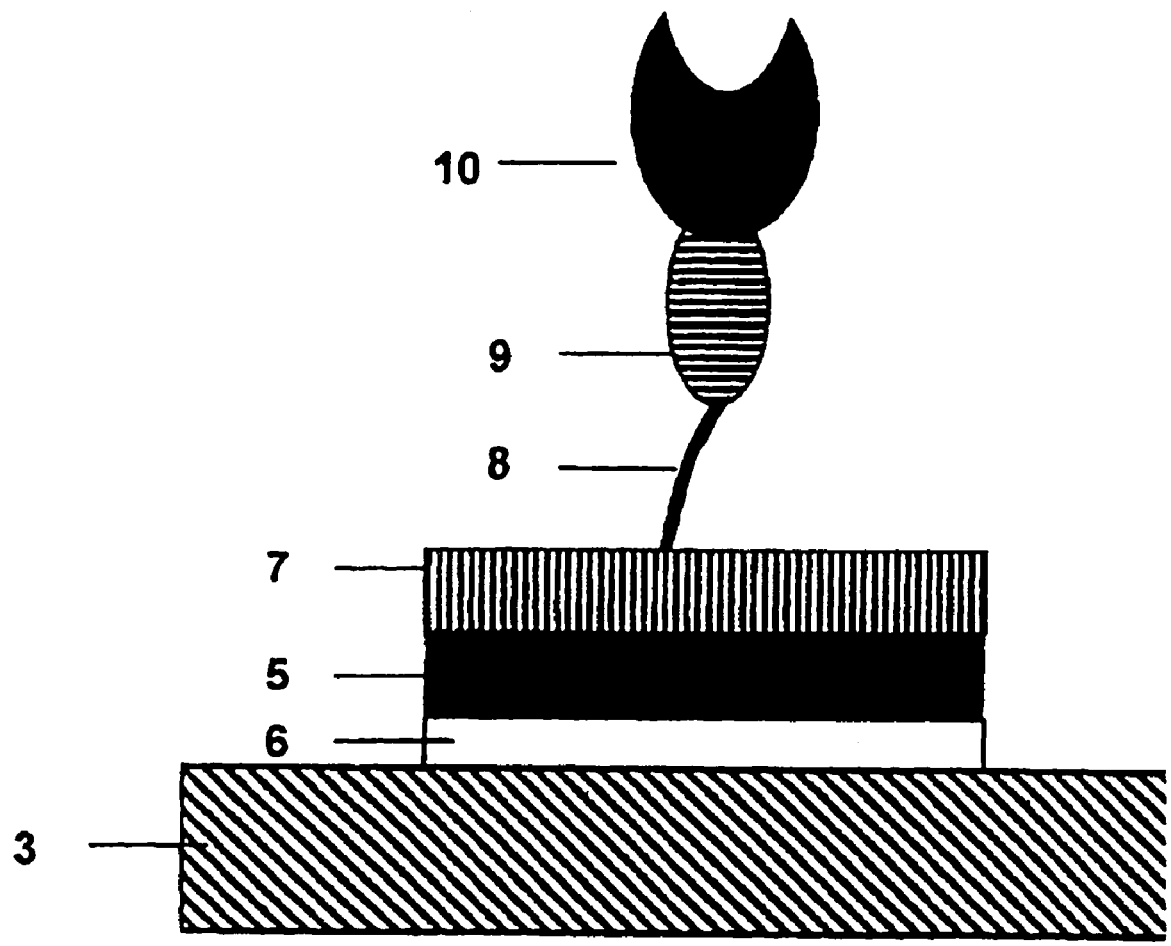
FIG. 7 shows the immobilization of a protein-capture agent on a monolayer-coated substrate via an affinity tag and an adaptor.

FIG. 7 shows a cross section of a patch on one particular embodiment of the invention array. The patch comprises a protein-capture agent 10 immobilized on a monolayer 7 via both an affinity tag 8 and an adaptor 9. The monolayer 7 rests on a coating 5. An interlayer 6 is used between the coating 5 and the substrate 3.

(f) Preparation of the Protein-Capture Agents of the Array.

The protein-capture agents used on the array may be produced by any of the variety of means known to those of ordinary skill in the art. In a preferred embodiment of the invention, the protein-capture agents are proteins, and in an especially preferred embodiment, the protein-capture agents are antibodies or antibody fragments. Therefore, methods of preparing these types of possible protein-capture agents are emphasized here.

In preparation for immobilization to the arrays of the present invention, the antibody moiety, or any other protein-capture agent which is a protein or polypeptide, can optionally be expressed from recombinant DNA either in vivo or in vitro. The cDNA of the antibody or antibody fragment or other protein-capture agent is cloned into an expression vector (many examples of which are commercially available) and introduced into cells of the appropriate organism for expression. A broad range of host cells and expression systems may be used to produce the antibodies and antibody fragments, or other proteins, which serve as the protein-capture agents on the array. Expression in vivo may be done in bacteria (for example. *Escherichia coli*), plants (for example, *Nicotiana tabacum*), lower eukaryotes (for example, *Saccharomyces cerevisiae, Saccharomyces pombe, Pichia pastoris*), or higher eukaryotes (for example, bacculovirus-infected insect cells, insect cells, mammalian cells). For in vitro expression PCR-amplified DNA sequences are directly used in coupled in vitro transcription/translation systems (for instance: *Escherichia coli* S30 lysates from T7 RNA polymerase expressing, preferably protease-deficient strains; wheat germ lysates; reticulocyte lysates (Promega, Pharmacia, Panvera)). The choice of organism for optimal expression depends on the extent of post-translational modifications (i.e., glycosylation, lipid-modifications) desired. The choice of expression system also depends on other issues, such as whether an intact antibody is to be produced or just a fragment of an antibody (and which fragment), since disulfide bond formation will be affected by the choice of a host cell. One of ordinary skill in the art will be able to readily choose which host cell type is most suitable for the protein-capture agent and application desired.

DNA sequences encoding affinity tags and adaptors can be engineered into the expression vectors such that the protein-capture agent genes of interest can be cloned in frame either 5' or 3' of the DNA sequence encoding the affinity tag and adaptor protein.

The expressed protein-capture agents are purified by affinity chromatography using commercially available resins.

Preferably, production of a plurality of protein-capture agents involves parallel processing from cloning to protein expression and protein purification. cDNAs for the protein-capture agent of interest will be amplified by PCR using cDNA libraries or expressed sequence tags (EST) clones as templates. For in vivo expression of the proteins, cDNAs can be cloned into commercial expression vectors (Qiagen, Novagen, Clontech) and introduced into an appropriate organism for expression (see above). For in vitro expression PCR-amplified DNA sequences are directly used in coupled in vitro transcription/translation systems (see above).

*Escherichia coli*-based protein expression is generally the method of choice for soluble proteins that do not require extensive post-translational modifications for activity.

Extracellular or intracellular domains of membrane proteins will be fused to protein adaptors for expression and purification.

The entire approach can be performed using 96-well assay plates. PCR reactions are carried out under standard conditions. Oligonucleotide primers contain unique restriction sites for facile cloning into the expression vectors. Alternatively, the TA cloning system (Clontech) can be used. The expression vectors contain the sequences for affinity tags and the protein adaptors. PCR products are ligated into the expression vectors (under inducible promoters) and introduced into the appropriate competent Escherichia coli strain by calcium-dependent transformation (strains include: XL-1 blue, BL21, SG13009(lon-)). Transformed Escherichia coli cells are plated and individual colonies transferred into 96-array blocks. Cultures are grown to mid-log phase, induced for expression, and cells collected by centrifugation. Cells are resuspended containing lysozyme and the membranes broken by rapid freeze/thaw cycles, or by sonication. Cell debris is removed by centrifugation and the supernatants transferred to 96-tube arrays. The appropriate affinity matrix is added, the protein-capture agent of interest is bound and nonspecifically bound proteins are removed by repeated washing steps using 12-96 pin suction devices and centrifugation. Alternatively, magnetic affinity beads and filtration devices can be used (Qiagen). The proteins are eluted and transferred to a new 96-well array. Protein concentrations are determined and an aliquot of each protein-capture agent is spotted onto a nitrocellulose filter and verified by Western analysis using an antibody directed against the affinity tag on the protein-capture agent. The purity of each sample is assessed by SDS-PAGE and Silver staining or mass spectrometry. The protein-capture agents are then snap-frozen and stored at −80° C.

Saccharomyces cerevisiae allows for the production of glycosylated protein-capture agents such as antibodies or antibody fragments. For production in Saccharomyces cerevisiae, the approach described above for Escherichia coli can be used with slight modifications for transformation and cell lysis. Transformation of Saccharomyces cerevisiae is by lithium-acetate and cell lysis is either by lyticase digestion of the cell walls followed by freeze-thaw, sonication or glass-bead extraction. Variations of post-translational modifications can be obtained by using different yeast strains (i.e., Saccharomyces prombe, Pichia pastoris).

One aspect of the bacculovirus system is the array of post-translational modifications that can be obtained, although antibodies and other proteins produced in bacculovirus contain carbohydrate structures very different from those produced by mammalian cells. The bacculovirus-infected insect cell system requires cloning of viruses, obtaining high titer stocks and infection of liquid insect cell suspensions (cells such as SF9, SF21).

Mammalian cell-based expression requires transfection and cloning of cell lines. Either lymphoid or non-lymphoid cell may be used in the preparation of antibodies and antibody fragments. Soluble proteins such as antibodies are collected from the medium while intracellular or membrane bound proteins require cell lysis (either detergent solubilization, freeze-thaw). The protein-capture agents can then be purified analogous to the procedure described for Escherichia coli.

For in vitro translation the system of choice is Escherichia coli lysates obtained from protease-deficient and T7 RNA polymerase overexpressing strains. Escherichia coli lysates provide efficient protein expression (30-50 µg/ml lysate). The entire process is carried out in 96-well arrays. Antibody genes or other protein-capture agent genes of interest are amplified by PCR using oligonucleotides that contain the gene-specific sequences containing a T7 RNA polymerase promoter and binding site and a sequence encoding the affinity tag. Alternatively, an adaptor protein can be fused to the gene of interest by PCR. Amplified DNAs can be directly transcribed and translated in the Escherichia coli lysates without prior cloning for fast analysis. The antibody fragments or other proteins are then isolated by binding to an affinity matrix and processed as described above.

Alternative in vitro translation systems which may be used include wheat germ extracts and reticulocvte extracts. In vitro synthesis of membrane proteins or post-translationally modified proteins will require reticulocyte lysates in combination with microsomes.

In one embodiment of the invention, the protein-capture agents on the array are monoclonal antibodies. The production of monoclonal antibodies against specific protein targets is routine using standard hybridoma technology. In fact, numerous monoclonal antibodies are available commercially. The preparation and use of an array of monoclonal antibodies is illustrated in the specific example, Example 8, below.

As an alternative to obtaining antibodies or antibody fragments by cell fusion or from continuous cell lines, the antibody moieties may be expressed in bacteriophage. Such antibody phage display technologies are well known to those skilled in the art. The bacteriophage expression systems allow for the random recombination of heavy- and light-chain sequences, thereby creating a library of antibody sequences which can be selected against the desired antigen. The expression system can be based on bacteriophage λ or, more preferably, on filamentous phage. The bacteriophage expression system can be used to express Fab fragments, Fv's with an engineered intermolecular distulfide bond to stabilize the $V_H$-$V_L$ pair (dsFv's), scFvs, or diabody fragments.

The antibody genes of the phage display libraries may be from pre-immunized donors. For instance, the phage display library could be a display library prepared from the spleens of mice previously immunized with a mixture of proteins (such as a lysate of human T-cells). Immunization can optionally be used to bias the library to contain a greater number of recombinant antibodies reactive towards a specific set of proteins (such as proteins found in human T-cells). Alternatively, the library antibodies may be derived from naive or synthetic libraries. The naive libraries have been constructed from spleens of mice which have not been contacted by external antigen. In a synthetic library, portions of the antibody sequence, typically those regions corresponding to the complementarity determining regions (CDR) loops, have been mutagenized or randomized.

The phage display method involves batch-cloning the antibody gene library into a phage genome as a fusion to the gene encoding one of the phage coat proteins (pIII, pVI, or pVIII). The pIII phage protein gene is preferred. When the fusion product is expressed it is incorporated into the mature phage coat. As a result, the antibody is displayed as a fusion on the surface of the phage and is available for binding and hence, selection, on a target protein. Once a phage particle is selected as bearing an antibody-coat protein fusion with the desired affinity towards the target protein, the genetic material within the phage particle which corresponds to the displayed antibody can be amplified and sequenced or otherwise analyzed.

In a preferred embodiment, a phagemid is used as the expression vector in the phage display procedures. A phagemid is a small plasmid vector that carries gene III with appropriate cloning sites and a phage packaging signal and contains both host and phage origins of replication. The phagemid is unable to produce a complete phage as the gene III fusion is the only phage gene encoded on the phagemid. A viable phage can be produced by infecting cells containing the phagemid with a helper phage containing a defective replication origin. A hybrid phage emerges which contains all of the helper phage proteins as well as the gene III-rAb fusion. The emergent phage contains the phagemid DNA only.

In a preferred embodiment of the invention, the recombinant antibodies used in phage display methods of preparing protein-capture agents for the arrays of the invention are expressed as genetic fusions to the bacteriophage gene III protein on a phagemid vector. For instance, the antibody variable regions encoding a single-chain Fv fragment can be fused to the amino terminus of the gene III protein on a phagemid. Alternatively, the antibody fragment sequence could be fused to the amino terminus of a truncated pIII sequence lacking the first two N-terminal domains. The phagemid DNA encoding the antibody-pIII fusion is preferably packaged into phage particles using a helper phage such as M13KO7 or VCS-M13, which supplies all structural phage proteins.

To display Fab fragments on phage, either the light or heavy (Fd) chain is fused via its C-terminus to pIII. The partner chain is expressed without any fusion to pIII so that both chains can associate to form an intact Fab fragment.

Any method of selection may be used which separates those phage particles which do bind the target protein from those which do not. The selection method must also allow for the recovery of the selected phages. Most typically, the phage particles are selected on an immobilized target protein. Some phage selection strategies known to those skilled in the art include the following: panning on an immobilized antigen; panning on an immobilized antigen using specific elution; using biotinylated antigen and then selecting on a streptavidin resin or streptavidin-coated magnetic beads; affinity purification; selection on Western blots (especially useful for unknown antigens or antigens difficult to purify); in vivo selection; and pathfinder selection. If the selected phage particles are amplified between selection rounds, multiple iterative rounds of selection may optionally be performed.

Elution techniques will vary depending upon the selection process chosen, but typical elution techniques include washing with one of the following solutions: HCl or glycine buffers; basic solutions such as triethylamine; chaotropic agents; solutions of increased ionic strength; or DTT when biotin is linked to the antigen by a disulfide bridge. Other typical methods of elution include enzymatically cleaving a protease site engineered between the antibody and gene III, or by competing for binding with excess antigen or excess antibodies to the antigen.

A method for producing an array of antibody fragments therefore comprises first selecting recombinant bacteriophage which express antibody fragments from a phage display library. The recombinant bacteriophage are selected by affinity binding to a protein which is an expression product, or fragment thereof, of a cell or population of cells in an organism. (Iterative rounds of selection are possible, but optional.) Next, at least one purified sample of an antibody fragment from a bateriophage which was selected in the first step is produced. This antibody production step typically entails infecting E. coli cells with the selected bacteriophage. In the absence of helper phage, the selected bacteriophage then replicate as expressive plasmids without producing phage progeny. Alternatively, the antibody fragment gene of the selected recombinant bacteriophage is isolated, amplified, and then expressed in a suitable expression system. In either case, following amplification, the expressed antibody fragment of the selected and amplified recombinant bacteriophage is isolated and purified. In a third step of the method, the earlier steps of phage display selection and purified antibody fragment production are repeated using affinity binding to different proteins which are expression products, or fragments thereof, of the same cell or population of cells as before until the desired plurality of purified samples of different antibodies with different binding pairs are produced. In a final step of the method, the antibody fragment of each different purified sample is immobilized onto an organic thinfilm on a separate patch on the surface of a substrate to form a plurality of patches of antibody fragments on discrete, known regions of the substrate surface covered by organic thinfilm.

For instance, to generate an antibody array with antibody fragments against known protein targets, open reading frames of the known protein targets identified in DNA databases are amplified by polymerase chain reaction and transcribed and translated in vitro to produce proteins on which a recombinant bacteriophage expressing single-chain antibody fragments are selected. Once selected, the antibody fragment sequence of the selected bacteriophage is amplified (typically using the polymerase chain method) and recloned into a desirable expression system. The expressed antibody fragments are purified and then printed onto organic thinfilms on substrates to form the high density arrays.

In another embodiment of the invention, a method for producing an array of protein-capture agents is provided which comprises first selecting protein-capture agents from a library of protein-capture agents, where the protein-capture agents are selected by their affinity binding to the proteins from a cellular extract or body fluid. Preferably, the proteins are from a cellular extract. The proteins from the cellular extract or body fluid would typically be immobilized prior to the selection step. Suitable methods of immobilization such as crosslinking of the proteins to a resin are well known to one of ordinary skill in the art. The next step of this method comprises producing a plurality of purified samples of the selected protein-capture agents. The protein-capture agent of each different purified sample is immobilized onto an organic thinfilm on a separate patch on the surface of a substrate to form a plurality of patches of protein-capture agents on discrete, known regions of the substrate surface covered by organic thinfilm.

This method of array preparation optionally also comprises the additional step of biasing the library of protein-capture agents by eliminating from the library, those protein-capture agents which bind certain proteins, such as the proteins of a second cellular extract, wherein the protein-capture agents which are eliminated are removed from the library by their binding affinity to those certain proteins. This step of biasing the library may optionally occur after the selection step by affinity binding to the protein, but more typically, it occurs prior to that selection step. The order of the selecting and biasing steps will depend on the nature of the selection and elution procedures used in the method. One of ordinary skill in the art will readily be able to determine an appropriate series of steps.

In one embodiment of the optional step of biasing the library of protein-capture agents, the library is biased to eliminate protein-capture agents that recognize common proteins or proteins of non-interest. This is typically achieved by passing the library over an affinity surface, such as a chromatography column, containing cross-linked proteins of non-interest. The "flowthrough" containing protein-capture agents that did not react with the affinity surface is collected. This procedure enriches the library for protein-capture agents which bind proteins of interest or proteins specific to the cell to be assayed. For instance, if the library is derived from a specific cell type such a a human T-cell, the library may optionally be biased by passing it over an affinity surface which contains proteins prepared from a lysate of human fibroblasts or bacterial proteins to enrich the library for protein-capture agents which bind proteins specifically present in fibroblasts.

In a preferred embodiment of the method of preparing the array of protein-capture agents described above, the protein-capture agents are antibody fragments displayed on the surface of recombinant bacteriophages and the library of protein-capture agents is a phage display library. Therefore, a method for producing an antibody array comprises first selecting recombinant bacteriophage expressing antibody fragments from a phage display library, where the bacteriophage are selected by affinity binding to immobilized proteins of a body fluid, or more preferably, a cellular extract. The next step of this method comprises producing a plurality of purified samples of antibody fragments expressed by the selected recombinant bacteriophage. Preferably, antibody fragments which specifically bind more than 1000 of the proteins of the cellular extract are produced in this manner. In a final step of the method, the antibody fragment of each different purified sample is immobilized onto an organic thinfilm on a separate patch on the surface of a substrate to form a plurality of patches of antibody fragments on discrete known regions of the substrate surface. One specific example of this method is outlined in Example 6, below. Again, this method optionally also comprises the additional step of biasing the phage display library by eliminating from the library those bacteriophage displaying antibody fragments which bind certain proteins, such as the proteins of a second cellular extract. The bacteriophage which are eliminated are removed from the library by the binding affinity of their displayed antibody fragments to the certain proteins.

For instance, a method of preparing an antibody array optionally begins with a phage display library prepared from RNA isolated from the spleens of mice previously immunized with a lysate of human T-cells. The phage library is then passed over a column or affinity surface comprising proteins from the lysates of background cells such as human fibroblasts which have been cross-linked to a surface or resin. The phage remaining in the flowthrough solution from the first column/affinity surface is then passed over a second affinity surface, such as a chromatography column, containing cross-linked proteins prepared from a lysate of human T-cells. The flowthrough solution from the second column/affinity surface is then discarded since this solution contains phage which displays recombinant antibodies that did not react with the second affinity surface. Phage which specifically react with the second affinity surface and remain bound to the second affinity surface are then collected by elution. Elution can be achieved by lowered pH (2.0), increased ionic strength, or proteolytic release by a specific proteolytic cut site genetically engineered between the displayed recombinant antibody and the gene III protein of the phage. In a next step of the method, the eluted phage are separated into isolated plaques by plating and then propagated as separate cultures. Periplasmic fractions from the separate cultures are prepared and the corresponding recombinant antibodies purified. The purified recombinant antibodies are then dispensed into separate patches on a 2-D array where they are immobilized onto an organic thinfilm.

Methods of preparing an array of protein-capture agents where the protein-capture agents have been selected against the proteins of a cellular extract, or a body fluid, create arrays of protein-capture agents where all of the binding partners of the arrays are not initially known. The primary information provided by binding of proteins to these types of arrays is contained in the pattern of protein abundance. Once interesting patches on an array have been identified by comparison of the protein expression pattern to that of a control (for instance, it may be observed that there is a significant increase in the amount of protein bound to a patch of the array following exposure of a cell to a certain set of conditions), the identity of the protein ligand binding to a particular patch on the array can be assessed by affinity purification of the protein ligand followed by microsequencing and/or mass spectrometry or the like.

An alternative method for producing an array of protein-capture agents comprises: selecting protein-capture agents from a library of protein-capture agents, wherein the protein-capture agents are selected by their binding affinity to proteins expressed by a cDNA expression library; producing a plurality of purified samples of the selected protein-capture agents; and immobilizing each different purified protein-capture agent onto an organic thinfilm on a separate patch on the surface of a substrate to form a plurality of patches on discrete, known regions of the substrate surface covered by organic thinfilm This method also optionally comprises the additional step of biasing the protein-capture agent library by eliminating from the library those protein-capture agents which bind certain proteins, such as the proteins of a cellular extract, wherein the protein-capture agents which are eliminated are removed from the library by their binding affinity to said certain proteins. In most cases, the proteins which are used to subtract protein-capture agents from the library of protein-capture agents would be immobilized. This step of biasing the library may optionally occur after the selection step by affinity binding to the proteins expressed by the cDNA expression library, but more typically, it occurs prior to that selection step. The order of these step will depend on the nature of the selection and elution steps. One of ordinary skill in the art will readily be able to determine an appropriate series of steps. In the optional step of biasing the library of protein-capture agents, the library is optionally biased to eliminate protein-capture agents that recognize common proteins or proteins of non-interest (as described above for a previous embodiment). Preferably, the method further comprises the additional step of identifying which individual selected protein-capture agents bind which individual proteins expressed by the cDNA expression library.

In another preferred embodiment of the the method, the protein-capture agents are antibody fragments displayed on the surface of recombinant bacteriophages and the library of protein-capture agents is a phage display library.

For instance, one example of a method of preparing an array of antibodies optionally begins with a phage display library prepared from RNA isolated from the spleens of mice previously immunized with a lysate of human T-cells. The phage library is then passed over a column or affinity surface comprising proteins from the lysates of background cells such as human fibroblasts which have been cross-linked to a surface or resin. The phage remaining in the flowthrough solution from the first column/affinity surface is then collected. A cDNA expression library derived from message RNA (mRNA) isolated from human T-cells is prepared in which the expressed proteins from the expression library are genetically fused with an expression tag (such as a six histidine tag). The library is expanded and the tagged proteins are collectively expressed and purified. The pool of purified, tagged proteins from the cDNA expression library is cross-linked to an affinity surface, such as a chromatography column. The phage display library which passed through the first affinity surface or column is passed over the affinity surface bearing the immobilized proteins of the cDNA expression library. The flowthrough solution containing phage displaying recombinant antibodies that did not react with the affinity surface is discarded. Phage which specifically react with the affinity surface are collected by elution achieved by lowering the pH (2.0). Cells from the cDNA expression library are plated and a filter lift of the colonies is made using nitrocellulose or charged nylon filters. Reactive sites on the filter are blocked with a standard blocking solution and the filters are probed with the selected bacteriophage eluted off of the second column. The phage are visualized by reaction with a monoclonal antibody recognizing the gene VIII coat protein of the bacteriophage, conjugated to alkaline phosphatase. Reactive sites on the filter are cut out and the phage eluted from the filter pieces and propagated separately. The eluted phage are separated into isolated plaques and then propagated as separate cultures. Periplasmic fractions from the separate cultures are prepared and the corresponding recombinant antibodies purified. The purified recombinant antibodies are then dispensed onto separate patches of organic thinfilm on a 2-D array. Samples are reacted with the array and protein ligands with interesting differential abundance patterns (when compared to a control) are identified. Colonies on the original plate corresponding to the phage-reactive sites on the filter are propagated and the plasmids containing the cDNA sequenced to identify the protein ligands reactive with the recombinant antibodies of the phage.

In the preparation of the arrays of the invention, phage display methods analogous to those used for antibody fragments may be used for protein-capture agents other than antibody fragments as long as the protein-capture agent is composed of protein and is of suitable size to be incorporated into the phagemid or alternative vector and expressed as a fusion with a bacteriophage coat protein. Phage display techniques using non-antibody libraries typically make use of some type of protein host scaffold structure which supports the variable regions. For instance, β-sheet proteins, α-helical handle proteins, and other highly constrained protein structures have been used as host scaffolds.

Alternative display vectors may also be used to produce the protein-capture agents, such as antibody moieties, which are printed on the arrays of the invention. Polysomes, stable protein-ribosome-mRNA complexes, can be used to replace live bacteriophage as the display vehicle for recombinant antibody fragments or other proteins (Hanes and Pluckthum, *Proc. Natl. Acad. Sci USA*, 94:4937-4942, 1997). The polysomes are formed by preventing release of newly synthesized and correctly folded protein from the ribosome. Selection of the polysome library is based on binding of the antibody fragments or other proteins which are displayed on the polysomes to the target protein. mRNA which encodes the displayed protein or antibody having the desired affinity for the target is then isolated. Larger libraries may be used with polysome display than with phage display.

In still another alternative method of preparing the protein-capture agents of the arrays of the invention, an alternative display method of selection such as lambda display (Mikawa el al., *J. Mol. Biol.*, 262:21-30, 1996), bacterial display (Georgiou et al., *Nat. Biotechnol.*, 15:29-34, 1997) or eukaryotic cell display may instead by used.

Furthermore, selection methods other than display methods may also be used in the preparation of protein-capture agents for the arrays of the invention. As indicated above, the protein-capture agents may be obtained by any in vitro or in vivo selection procedure known to those skilled in the art. In one embodiment of the invention, protein-capture agents other than antibodies and antibody fragments are batch selected on the protein in cellular extracts. Such procedures generate a diversity of protein-capture agents which are highly suitable for applications in proteomics.

In alternative embodiments of the invention, the protein-capture agents are partially or wholly prepared by synthetic means. If the protein-capture agent is a protein, then methods of peptide synthetic or protein ligation may optionally be used to construct a protein from amino acid or polypeptide building blocks. Protein-capture agents which are polynucleotides are readily prepared synthetically.

(g) Uses of the Arrays.

The present invention also provides methods of using the invention arrays. In general, for a variety of applications including proteomics and diagnostics, the methods of the invention involve the delivery of the sample containing the proteins to be analyzed to the arrays. After the proteins of the sample have been allowed to interact with and become immobilized on the patches of the array comprising protein-capture agents with the appropriate biological specificity, the presence and/or amount of protein bound at each patch is then determined.

Use of one of the protein-capture agent arrays of the invention may optionally involve placing the two-dimensional array in a flowchamber with approximately 1-10 microliters of fluid volume per 25 mm$^2$ overall surface area. The cover over the array in the flowchamber is preferably transparent or translucent. In one embodiment, the cover may comprise Pyrex or quartz glass. In other embodiments, the cover may be part of a detection system that monitors interaction between the protein-capture agents immobilized on the array and protein in a solution such as a cellular extract. The flowchambers should remain filled with appropriate aqueous solutions to preserve protein activity. Salt, temperature, and other conditions are preferably kept similar to those of normal physiological conditions. Proteins in a fluid solution may be flushed into the flow chamber as desired and their interaction with the immobilized protein-capture agents determined. Sufficient time must be given to allow for binding between the protein-capture agent and its binding partner to occur. The amount of time required for this will vary depending upon the nature and tightness of the affinity of the protein-capture agent for its binding partner. No specialized microfluidic pumps, valves, or mixing techniques are required for fluid delivery to the array.

Alternatively, protein-containing fluid can be delivered to each of the patches of the array individually. For instance, in one embodiment, the regions of the substrate surface may be microfabricated in such a way as to allow integration of the array with a number of fluid delivery channels oriented perpendicular to the array surface, each one of the delivery channels terminating at the site of an individual protein-capture agent-coated patch.

The sample which is delivered to the array will typically be a fluid. In a preferred embodiment of the invention, the sample is a cellular extract or a body fluid. The sample to be assayed may optionally comprise a complex mixture of proteins, including a multitude of proteins which are not binding partners of the protein-capture agents of the array. If the proteins to be analyzed in the sample are membrane proteins, then those proteins will typically need to be solubilized prior to administration of the sample to the array. If the proteins to be assayed in the sample are proteins secreted by a population of cells in an organism, a sample which is derived from a body fluid is preferred. If the proteins to be assayed in the sample are intracellular, a sample which is a cellular extract is preferred. In one embodiment of the invention, the array may comprise protein-capture agents which bind fragments of the expression products of a cell or population of cells in an organism. In such a case, the proteins in the sample to be assayed may have been prepared by performing a digest of the protein in a cellular extract or a body fluid. In an alternative application of the array, the proteins from only specific fractions of a cell are collected for analysis in the sample.

In general, delivery of solutions containing proteins to be bound by the protein-capture agents of the array may optionally be preceded, followed, or accompanied by delivery of a blocking solution. A blocking solution contains protein or another moiety which will adhere to sites of non-specific binding on the array. For instance, solutions of bovine serum albumin or milk may be used as blocking solutions.

It is understood that some proteins a sample which are not the intended binding partner of the protein-capture agents of a patch (and may, in fact, be the intended binding partner of another patch) on the array may still bind to the patch to some degree. Preferably, this type of binding only occurs to a very minor degree. Also, it is understood that even when the correct binding partners are present in the solution being assayed, the binding partners will bind to the patch comprising their protein-capture agent with less than 100% efficiency.

A wide range of detection methods is applicable to the methods of the invention. As desired, detection may be either quantitative or qualitative. The invention array can be interfaced with optical detection methods such as absorption in the visible or infrared range, chemoluninescence, and fluorescence (including lifetime, polarization, fluorescence correlation spectroscopy (FCS), and fluorescence-resonance energy transfer (FRET)). Furthermore, other modes of detection such as those based on optical waveguides PCT Publication (WO 96/26432 and U.S. Pat. No. 5,677,196), surface plasmon resonance, surface charge sensors, and surface force sensors are compatible with many embodiments of the invention. Alternatively, technologies such as those based on Brewster Angle microscopy (BAM) (Schaaf et al., *Langmuir*, 3:1131-1135 (1987)) and ellipsometry (U.S. Pat. Nos. 5,141,311 and 5,116,121; Kim, *Macromolecules*, 22:2682-2685 (1984)) could be applied. Quartz crystal microbalances and desorption processes (see for example, U.S. Pat. No. 5,719,060) provide still other alternative detection means suitable for at least some embodiments of the invention array. An example of an optical biosensor system compatible both with some arrays of the present invention and a variety of non-label detection principles including surface plasmon resonance, total internal reflection fluorescence (TIRF), Brewster Angle microscopy, optical waveguide lightmode spectroscopy (OWLS), surface charge measurements, and ellipsometry can be found in U.S. Pat. No. 5,313,264.

Although non-label detection methods are generally preferred, some of the types of detection methods commonly used for traditional immunoassays which require the use of labels may be applied to the arrays of the present invention. These techniques include noncompetitive immunoassays, competitive immunoassays, and dual label, ratiometric immunoassays. These particular techniques are primarily suitable for use with the arrays of protein-capture agents when the number of different protein-capture agents with different specificity is small (less than about 100). In the competitive method, binding-site occupancy is determined indirectly. In this method, the protein-capture agents of the array are exposed to a labeled developing agent, which is typically a labeled version of the analyte or an analyte analog. The developing agent competes for the binding sites on the protein-capture agent with the analyte. The fractional occupancy of the protein-capture agents on different patches can be determined by the binding of the developing agent to the protein-capture agents of the individual patches. In the noncompetitive method, binding site occupancy is determined directly. In this method, the patches of the array are exposed to a labeled developing agent capable of binding to either the bound analyte or the occupied binding sites on the protein-capture agent. For instance, the developing agent may be a labeled antibody directed against occupied sites (i.e., a "sandwich assay"). Alternatively, a dual label, ratiometric, approach may be taken where the protein-capture agent is labeled with one label and the second, developing agent is labeled with a second label (Ekins, et al., *Clinica Chimica Acta.,* 194:91-114, 1990). Many different labeling methods may be used in the aforementioned techniques, including radioisotopic, enzymatic, chemiluminescent, and fluorescent methods. Fluorescent methods are preferred.

Figure 8:
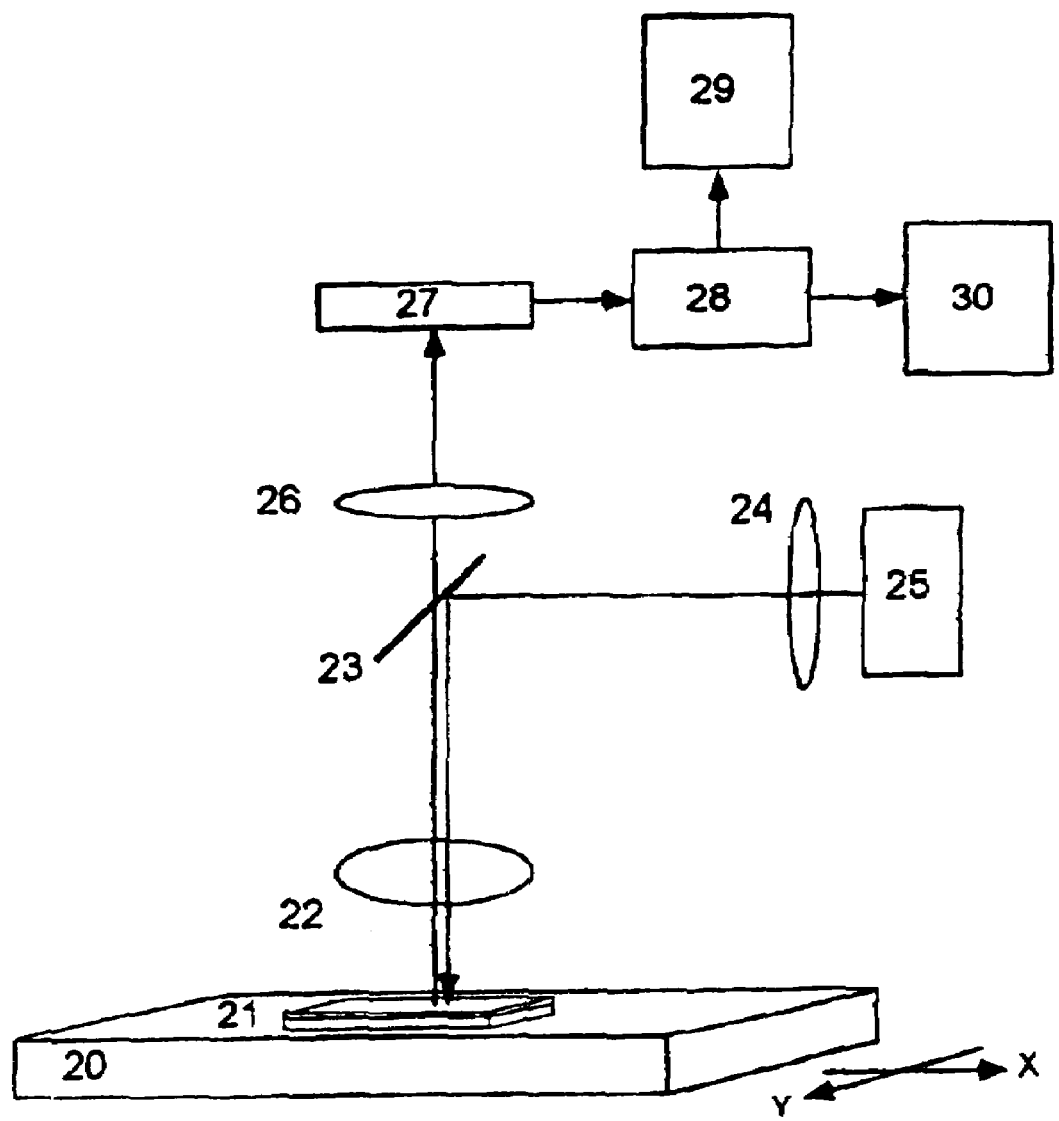
FIG. 8 shows a schematic of a fluorescence detection unit which may be used to monitor binding of proteins by the protein-capture agents of the array.

FIG. 8 shows a schematic diagram of one type of fluorescence detection unit which may be used to monitor interaction of immobilized protein-capture agents of an array with a protein analyte. In the illustrated detection unit, the array of protein-capture agents 21 is positioned on a base plate 20. Light from a 100W mercury arc lamp 25 is directed through an excitation filter 24 and onto a beam splitter 23. The light is then directed through a lens 22, such as a Micro Nikkor 55 mm 1:2:8 lens, and onto the array 21. Fluorescence emission from the array returns through the lens 22 and the beam splitter 23. After next passing through an emission filter 26, the emission is received by a cooled CCD camera 27, such as the Slowscan TE/CCD-1024SF&SB (Princeton Instruments). The camera is operably connected to a CPU 28 which is in turn operably connected to a VCR 29 and a monitor 30.

Figure 9:
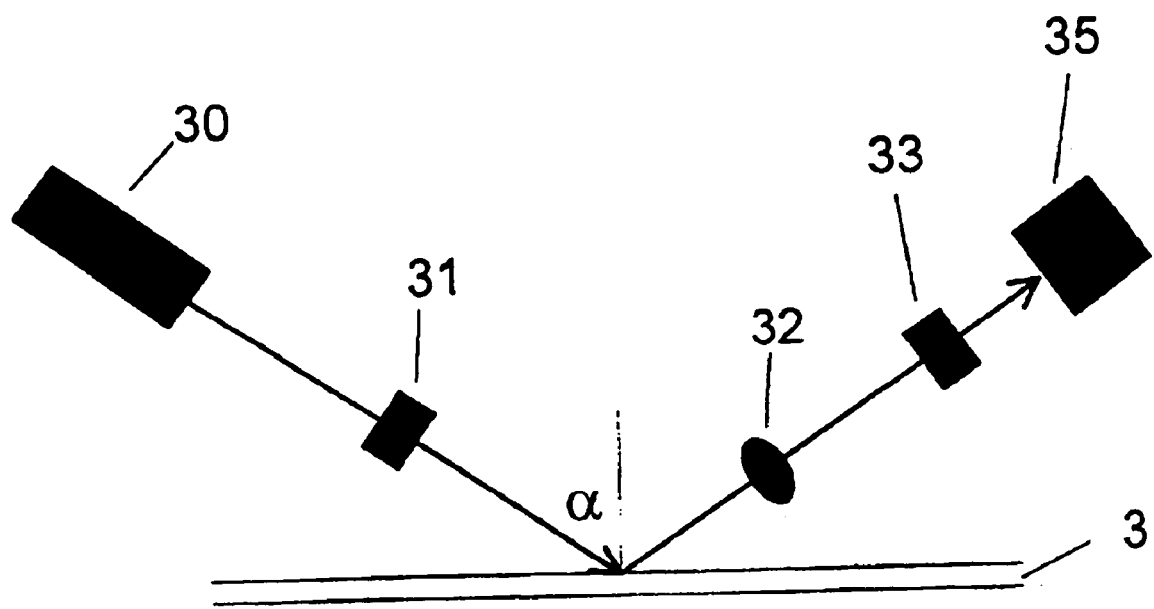
FIG. 9 shows a schematic of an ellipsometric detection unit which may be used to monitor binding of proteins by the protein-capture agents of the array.

FIG. 9 shows a schematic diagram of an alternative detection method based on ellipsometry. Ellipsometry allows for information about the sample to be determined from the observed change in the polarization state of a reflected light wave. Interaction of a protein analyte with a layer of immobilized protein-capture agents on a patch results in a thickness change and alters the polarization status of a plane-polarized light beam reflected off the surface. This process can be monitored in situ from aqueous phase and, if desired, in imaging mode. In a typical setup, monochromatic light (e.g. from a He—Ne laser, 30) is plane polarized (polarizer 31) and directed onto the surface of the sample and detected by a detector 35. A compensator 32 changes the elliptically polarized reflected beam to plane-polarized. The corresponding angle is determined by an analyzer 33 and then translated into the ellipsometric parameters Psi and Delta which change upon binding of protein with the protein-capture agents. Additional information can be found in Azzam, et al., *Ellipsometry and Polarized Light*, North-Holland Publishing Company: Amsterdam, 1977.

The arrays of the present invention are particularly useful for proteomics. Those arrays which comprise significant numbers of protein-capture agents of different specificity on separate patches can bind significant numbers of proteins which are expression products, or fragments thereof, of a cell or population of cells in an organism and are particularly suitable for use in applications involving proteomics. For instance, an array with at least about $10^3$ and up to about $10^5$ different protein-capture agents such as antibodies or antibody fragments can provide a highly comprehensive picture of the protein content of the cell under a specific set of conditions.

In one embodiment of the invention, a method of assaying in parallel for a plurality of different proteins in a sample which are expression products, or fragments thereof, of a cell or a population of cells in an organism, is provided which comprises the following steps: first, delivering the sample to an array of spatially distinct patches of different protein-capture agents under conditions suitable for protein binding, wherein each of the proteins being assayed is a binding partner of the protein-capture agent of at least one patch on the array; next, optionally washing said array to remove unbound or nonspecifically bound components of the sample from the array; and in a final step, detecting, either directly or indirectly, for the presence or amount of protein bound to each patch of the array.

In another embodiment of the invention, a method of assaying in parallel for a plurality of different proteins in a sample which are expression products, or fragments thereof, of a cell or a population of cells in an organism, comprises first delivering the sample to the invention array of protein-capture agents under conditions suitable for protein binding, wherein each of the proteins being assayed is a binding partner of the protein-capture agent of at least one patch on the array. The first step may be followed by an optional step of washing the array with fluid to remove unbound or nonspecifically bound components of the sample -from the array. Lastly, the presence or amount of protein bound to each patch is detected, either directly or indirectly.

A variety of different embodiments of the invention array of protein-capture agents may be used in the methods for assaying in parallel for a plurality of different proteins in a sample which are expression products, or fragments thereof, of a cell or a population of cells in an organism. Generally, preferred embodiments of these methods comprise the use of preferred arrays of the invention. For instance, in preferred embodiments of the method, the protein-capture agents are antibodies or antibody fragments. In further preferred embodiments for assaying the different amounts of a plurality of proteins in a cell in parallel or the protein expression pattern of a cell, the plurality of patches on the array can bind at least about 100 or at least about $10^3$ different proteins which are the expression products, or fragments thereof, of a cell or population of cells in an organism. Alternatively, the plurality of patches on the array used in the methods can bind at least about $10^4$ different proteins which are the expression products, or fragments thereof, of a cell or population of cells in an organism.

The methods of assaying in parallel for a plurality of different proteins in a sample which are expression products, or fragments thereof, of a cell or a population of cells in an organism, optionally comprise the additional step of further characterizing the protein bound to at least one patch of the array. This step is typically designed to identify the nature of the protein bound to the protein-capture agent of a particular patch. In some cases, the entire identity of the bound protein may not be known and the purpose of the further characterization may be the initial indentification of the mass, sequence, structure and/or activity of the bound protein. In other cases, the basic identity of the protein may be known, but the post-translational modification, activation state, or some other feature of the protein may not be known. In one embodiment, the step of further characterizing the proteins involves measuring the activity of the proteins. Although in some cases it may be preferable to remove the protein from the patch before the step of further characterizing the protein is carried out, in other cases the protein can be further characterized while still bound to the patch. In still further embodiments, the protein-capture agents of the patch which binds a protein can be used to isolate and/or purify the protein from cells. The purified sample can then be characterized through traditional means such as microsequencing, mass spectrometry, and the like.

In another embodiment, the present invention provides a method of determining the protein expression pattern of a cell or population of cells in an organism. This method involves first delivering a sample containing expression products, or fragments thereof, of the cell or population of cells to the protein-capture agent array of the invention under conditions suitable for protein binding. The presence and/or amount of protein bound to each patch can then be determined by a suitable detection means. The detection may be either direct or indirect. Quantitative detection is typically preferred for this application (and for other proteomics applications). The method preferably further comprises an additional step before the detection step comprising washing the array to remove unbound or nonspecifically bound components of the sample from the array. The amount of protein bound to a patch of the array may optionally be determined relative to the amount of a second protein bound to a second patch of the array. The method of determining the protein expression pattern of a cell or a population of cells in an organism, optionally comprises the additional step of further characterizing the proteins bound to at least one patch of the array, as previously described above.

In the method of assaying the protein expression pattern of a cell or population of cells in an organism, many of the targets of the protein-capture agents of the array may optionally be of unknown sequence, identity, and/or function. For instance, the antibodies of the array may have been prepared by selecting a phage display library by affinity binding to the immobilized proteins of a cellular extract which contains many unidentified proteins. If the protein bound by a protein-capture agent on a particular patch of an array is unknown, but is of interest, then that protein may optionally be later identified or characterized by first using the same protein-capture agent that was used on the array to isolate the protein in question from cells. The isolated binding partner from the cell can then be assayed directly for function and/or sequenced.

The arrays of protein-capture agents may also be used to compare the protein expression patterns of two cells or populations of cells. In this method, a sample containing expression products, or fragments thereof, of a first cell or population of cells is delivered to the invention array of protein-capture agents under conditions suitable for protein binding. In an analogous manner, a sample containing expression products, or fragments thereof, of a second cell or population of cells to a second array, is delivered to a second array which is identical to the first array. Preferably, both arrays are then washed to remove unbound or nonspecifically bound components of the sample from the arrays. In a final step, the amounts of protein remaining bound to the patches of the first array are compared to the amounts of protein remaining bound to the corresponding patches of the second array. If it is desired to determine the differential protein expression pattern of two cells or populations of cells, for instance, then the amount of protein bound to the patches of the first array may be subtracted from the amount of protein bound to the corresponding patches of the second array.

Methods of comparing the protein expression of two cells or populations of cells are particularly useful for the understanding of biological processes. For instance, using these methods, the protein expression patterns of identical cells or closely related cells exposed to different conditions can be compared. Most typically, the protein content of one cell or population of cells is compared to the protein content of a control cell or population of cells. For instance, in one embodiment of the invention, one of the cells or populations of cells is neoplastic and the other cell is not. In another embodiment, one of the two cells or populations of cells being assayed is infected with a pathogen. Alternatively, one of the two cells or populations of cells has been exposed to a stressor and the other cell or population of cells serves as a control. The stressor may optionally be chemical, environmental, or thermal. One of the two cells may optionally be exposed to a drug or a potential drug and its protein expression pattern compared to a control cell.

Such methods of assaying differential gene expression at the protein level are useful in the identification and validation of new potential drug targets as well as for drug screening. For instance, the method may be used to identify a protein which is overexpressed in tumor cells, but not in normal cells. This protein may be a target for drug intervention. Inhibitors to the action of the overexpressed protein can then be developed. Alternatively, antisense strategies to inhibit the overexpression may be developed. In another instance, the protein expression pattern of a cell, or population of cells, which has been exposed to a drug or potential drug can be compared to that of a cell, or population of cells, which has not been exposed to the drug. This comparison will provide insight as to whether or not the drug has had the desired effect on a target protein (drug efficacy) and whether other proteins of the cell, or population of cells, have also been affected (drug specificity).

The arrays of the present invention are also suitable for diagnostic applications and suitable for use in diagnostic devices. The high density of the antibodies on some arrays of the present invention enables a large number of different, antibody-based diagnostic tests to be formatted onto a single biochip. The protein-capture agents on the invention array can be used to evaluate the status of a disease condition in a tissue, such as a tumor, where the expression levels of certain proteins in the cells of the tissue is known to be indicative of a particular type of disease condition or stage of a disease condition. If certain patterns of protein expression are not previously known to be indicative of a disease state, the protein-capture agent arrays of the invention can then first be used to establish this information.

Accordingly, in one embodiment, the invention provides a method of evaluating a disease condition in a tissue of an organism comprising first contacting the invention array of protein-capture agents with a sample comprising the expression products, or fragments thereof, of the cells of the tissue being evaluated, wherein the contacting occurs under conditions suitable for protein binding and wherein the binding partners of a plurality of protein-capture agents on the array include proteins which are expression products, or fragment thereof, of the cells of the tissue and whose expression levels are indicative of the disease condition. The method next comprises detecting, either directly or indirectly, for the presence of protein to each patch. In a preferred embodiment, the method further comprises the step of washing the array to remove unbound or nonspecifically bound components of the sample from the array. In such a method, the array will typically comprise protein-capture agents which bind those proteins whose presence, absence, or relative amount in cells is known to be indicative of a particular type of disease condition or state of a disease condition. For instance, the plurality of proteins being assayed in such a method may include such proteins as HER2 protein or prostate-specific antigen (PSA).

(h) EXAMPLES

The following specific examples are intended to illustrate the invention and should not be construed as limiting the scope of the claims:

Example 1

Fabrication of a Two-Dimensional Array by Photolithography

In a preferred embodiment of the invention, two-dimensional arrays are fabricated onto the substrate material via standard photolithography and/or thin film deposition. Alternative techniques include microcontact printing. Usually, a computer-aided design pattern is transferred to a photomask using standard techniques, which is then used to transfer the pattern onto a silicon wafer coated with photoresist.

In a typical example, the array ("chip") with lateral dimensions of 10×10 mm comprises squared patches of a bioreactive layer (here: gold as the coating on a silicon substrate) each 0.1×0.1 mm in size and separated by hydrophobic surface areas with a 0.2 mm spacing, 4" diameter Si(100) wafers (Virginia Semiconductor) are used as bulk materials. Si(100) wafers are first cleaned in a 3:1 mixture of $H_2SO_4$, conc.: 30% $H_2O_2$ (90° C. 10 min). rinsed with deionized water (18 MΩcm), finally passivated in 1% aqueous HF, and singed at 150° C. for 30 min to become hydrophobic. The wafer is then spincoated with photoresist (Shipley 1813), prebaked for 25 minutes at 90° C., exposed using a Karl Suss contact printer and developed according to standard protocols. The wafer is then dried and postbaked at 110° C. for 25 min. In the next step, the wafer is primed with a titanium layer of 20 nm thickness followed by a 200 nm thick gold layer. Both layers were deposited using electron-beam evaporation (5 Å/s). After resist stripping and a short plasma treatment, the gold patches can be further chemically modified to achieve the desired bioreactive and biocompatible properties (see Example 3, below).

Example 2

Fabrication of a Two-Dimensional Array by Deposition through a Hole Mask

In another preferred embodiment the array of gold patches is fabricated by thin film deposition through a hole mask which is in direct contact with the substrate. In a typical example, Si(100) wafers are first cleaned in a 3:1 mixture of $H_2SO_4$, conc.: 30% $H_2O_2$ (90° C., 10 min), rinsed with deionized water (18 MΩcm), finally passivated in 1% aqueous HF and singed at 150° C. for 30 min to become hydrophobic. The wafer is then brought into contact with a hole mask exhibiting the positive pattern of the desired patch array. In the next step, the wafer is primed with a titanium layer of 20 nm thickness, followed by a 200 nm thick gold layer. Both layers were deposited using electron-beam evaporation (5 Å/s). After removal of the mask, the gold patches can be further chemically modified to achieve the desired bioreactive and biocompatible properties (see Example 3, below).

Example 3

Synthesis of an Aminoreactive Monolayer Molecule (Following the Procedure Outlined in Wagner el al, *Biophys. J.*, 1996, 70:2052-2066)

General. $^1$H- and $^{13}$C-NMR spectra are recorded on Bruker instruments (100 to 400 MHz). Chemical shifts (δ) are reported in ppm relative to internal standard ((CH$_3$)$_4$Si, δ=0.00 ($^1$H- and $^{13}$C-NMR)). FAB-mass spectra are recorded on a VG-SABSEQ instrument (Cs$^+$, 20 keV). Transmission infrared spectra are obtained as dispersions in KBr on an FTIR Perkin-Elmer 1600 Series instrument. Thin-layer chromatography (TLC) is performed on pre-coated silica gel 60 F254 plates (MERCK, Darmstadt, FRG), and detection was done using Cl$_2$/toluidine, PdCl$_2$ and UV-detection under NH$_3$-vapor. Medium pressure liquid chromatography (MPLC) is performed on a Labomatic MD-80 (LABOMATIC INSTR. AG, Allschwil, Switzerland) using a Buechi column (460×36 mm; BUECHI, Flawil, Switzerland), filled with silica gel 60 (particle size 15-40 μm) from Merck.

Synthesis of 11,11'-dithiobis(succinimidylundecanoate) (DSU). Sodium thiosulfate (55.3 g, 350 mmol) is added to a suspension of 11-bromo-undecanoic acid (92.8 g, 350 mmol) in 50% aqueous 1,4-dioxane (1000 ml). The mixture is heated at reflux (90° C.) for 2 h until the reaction to the intermediate Bunte salt was complete (clear solution). The oxidation to the corresponding disulfide is carried out in situ by adding iodine in portions until the solution retained with a yellow to brown colour. The surplus of iodine is retitrated with 15% sodium pyrosulfite in water. After removal of 1,4-dioxane by rotary evaporation the creamy suspension is filtered lo yield product 11,11'-dithiobis(undecanoic acid). Recrystallization from ethyl acetate/THF provides a white solid (73.4 g. 96.5%): mp 94° C.; $^1$H NMR (400 MHz, CDCl$_3$/CD$_3$OD 95:5): δ2.69 (t, 2H, J=7.3 Hz), 2.29 (t, 2H, J=7.5 Hz), 1.76-1.57 (m, 4H), and 1.40-1.29 (m, 12H); FAB-MS (Cs$^+$, 20 keV): m/z (relative intensity) 434 (100, M$^+$). Anal. Calcd. for C$_{22}$H$_{42}$O$_4$S$_2$: C, 60.79; H, 9.74; S, 14.75. Found: C, 60.95; H, 9.82; S, 14.74. To a solution of 11,11'-dithiobis(undecanoic acid) (1.0 g, 2.3 mmol) in THF (50 ml) is added N-hydroxysuccinimide (0.575 g, 5 mmol) followed by DCC (1.03 g, 5 mmol) at 0° C. After the reaction mixture is allowed to warm to 23° C. and is stirred for 36 h at room temperature, the dicyclohexylurea (DCU) is filtered. Removal of the solvent under reduced pressure and recrystallization from acetone/hexane provides 11,11'-dithiobis(succinimidylundecanoate) as a white solid. Final purification is achieved by medium pressure liquid chromatography (9 bar) using silica gel and a 2:1 mixture of ethyl acetate and hexane. The organic phase is concentrated and dried in vacuum to afford 11,11'-dizthiobis(succinimidylundecanoate) (1.12 g, 78%): mp 95° C.; $^1$H NMR (400 MHz, CDCl$_3$): δ 2.83 (s, 4H), 2.68 (t, 2H, J=7.3 Hz), 2.60 (t, 2H, J=7.5 Hz), 1.78-1.63 (m, 4H), and 1.43-1.29 (m, 12H); FAB-MS (Cs$^+$, 20 keV): m/z (relative intensity) 514 (100), 628 (86, M$^+$). Anal. Calcd. for C$_{30}$H$_{48}$N$_2$O$_8$S$_2$: C, 57.30; H, 7.69; N, 4.45; S, 10.20. Found: C, 57.32; H, 7.60; N, 4.39; S, 10.25.

Example 4

Formation of an Aminoreactive Monolayer on Gold (Following the Procedure of Wagner el al., *Biophys. J.*, 1996. 70:2052-2066)

Monolayers based on 11,11'-dithiobis(succinimidylundecanoate) (DSU) can be deposited on Au(111) surfaces of substrates described under Examples 1 and 2 by immersing them into a 1 mM solution of DSU in chloroform at room temperature for 1 hour. After rinsing with 10 volumes of solvent, the N-hydroxysuccinimidyl-terminated monolayer is dried under a stream of nitrogen and immediately used for immobilizition of the protein-capture agents.

Example 5

Formation and use of an Array of Immobilized Fab' Antibody Fragments to Detect Concentrations of Soluble Proteins Prepared from Cultured Mammalian Cells Collections of IgG antibodies are purchased from commercial sources (e.g. Pierce, Rockford, Ill.). The antibodies are first purified by affinity chromatography based on binding to immobilized protein A. The antibodies are diluted 1:1 in binding buffer(0.1 M Tris-HCl, 0.15 M NaCl, pH 7.5). A 2 ml minicolumn containing a gel with immobilized protein A is prepared. (Hermanson, et. al., *Immobilized Affinity Ligand Techniques*, Academic Press, San Diego, 1992.) The column is equilibrated with 10 ml of binding buffer. Less than 10 mg of immunoglobulin is applied to each 2 ml minicolumn and the column is washed with binding buffer until the absorbance at 280 nm is less than 0.02. The bound immunoglobulins are eluted with 0.1 M glycine, 0.15 M NaCl, pH 2.8, and immediately neutralized with 1.0 M Tris-HCl, pH 8.0 to 50 mM final concentration and then dialyzed against 10 mM sodium phosphate, 0.15 M NaCl, pH 7.2 and stored at 4° C.

The purified immunoglobulin are digested with immobilized pepsin. Pepsin is an acidic endopeptidase and hydrolyzes proteins favorably adjaent to aromatic and dicarboxylic L-amino acid residues. Digestion of IgG with pepsin generates intact F(ab')$_2$ fragments. Immobilized pepsin gel is washed with digestion buffer; 20 mM sodium acetate. pH 4.5. A solution of purified IgG at 10 mg/ml is added to the immobilized pepsin gel and incubated at 37° C. for 2 hours. The reaction is neutralized by the addition of 10 mM Tris-HCl. pH 7.5 and centrifuged to pellet the gel. The supernatant liquid is collected and applied to an immobilized protein A column, as described above, to separate the F(ab')$_2$ fragments from the Fc and undigested IgG. The pooled F(ab')$_2$ is dialyzed against 10 mM sodium phosphate, 0.15 M NaCl, pH 7.2 and stored at 4° C. The quantity of pooled, eluted F(ab')$_2$ is measured by peak area absorbance at 280 nm.

The purified F(ab')$_2$ fragments at a concentration of 10 mg/ml are reduced at 37° C. for 1 hour in a buffer of 10 mM sodium phosphate, 0.15 M NaCl, 10 mM 2-mercaptoethylamine, 5 mM EDTA, pH 6.0. The Fab' fragments are separated from unsplit F(ab')$_2$ fragments and concentrated by application to a Sephadex G-25 column (M$_r$=46,000-58,000). The pooled Fab' fragments are dialyzed against 10 mM sodium phosphate, 0.15 M NaCl, pH 7.2. The reduced Fab' fragments are diluted to 100 μg/ml and applied onto the bioreactive patches containing exposed aminoreactive functional groups using a computer-aided, capillary-based microdispensing system (for antibody immobilization procedures, see Dammer et al., *Biophys. J.*, 70:2437-2441, 1996). After an immobilization period of 30 minutes at 30° C. the array is rinsed extensively with 10 mM sodium phosphate. 0.15 M NaCl. 5 mM EDTA. pH 7.0.

Transformed human cells grown in culture are collected by low speed centrifugation, briefly wished with ice-cold phosphate-buffered solution (PBS), and then resuspended in ice-cold hypotonic buffer containing DNase/RNase (10 µg/ml each, final concentration) and a mixture of protease inhibitors. Cells are transferred to a microcentrifuge tube, allowed to swell for 5 minutes, and lysed by rapid freezing in liquid nitrogen and thawing in ice-cold water. Cell debris and precipitates are removed by high-speed centrifugation and the supernatant is cleared by passage through a 0.45 µm filter. The cleared lysate is applied to the Fab' fragment array described above and allowed to incubate for 2 hours at 30° C. After binding the array is washed extensively with 10 mM sodium phosphate, 0.15 M NaCl, 5 mM EDTA, pH 7.0. The location and amount of bound proteins are determined by optical detection.

Example 6

Formation and use of an Array of Immobilized Antibody Fragments to Detect Concentrations of Soluble Proteins Prepared from Cultured Mammalian Cells A combinatorial library of filamentous phage expressing scFv antibody fragments is generated based on the technique of McCafferty and coworkers; McCafferty, et al., *Nature*, 1990, 348:552-554; Winter and Milstein, *Nature*, 1991, 349:293-299. Briefly, mRNA is purified from mouse spleens and used to construct a cDNA library. PCR fragments encoding sequences of the variable heavy and light chain immunoglobulin genes of the mouse are amplified from the prepared cDNA. The amplified PCR products are joined by a linker region of DNA encoding the 15 amino acid peptide ($Gly_4SerGly_2CysGlySerGly_4Ser$) (SEQ ID NO: 1) and the resulting full-length PCR fragment is cloned into an expression plasmid (pCANTAB 5 E) in which the purification peptide tag (E Tag) has been replaced by a $His_6$ peptide (SEQ ID NO: 2). Electrocompetent TGl *E. coli* cells are transformed with the expression plasmid by electroporation. The pCANTAB-transformed cells are induced to produced functional filamentous phage expressing scFv fragments by superinfection with M13KO7 helper phage. Cells are grown on glucose-deficient medium containing the antibiotics ampicillin (to select for cells with the phageinid) and kanamycin (to select for cells infected with M13KO7). In the absence of glucose, the lac promoter present on the phagemid is no longer repressed, and synthesis of the scFv-gene 3 fusion begins.

Proteins from a cell lysate are adsorbed to the wells of a 96-well plate. Transformed human cells grown in culture are collected by low speed centrifugation and the cells are briefly washed with ice-cold PBS. The washed cells are then resuspended in ice-cold hypotonic buffer containing DNasae/RNase (10 µg/ml each, final concentration) and a mixture of protease inhibitors, allowed to swell for 5 minutes, and lysed by rapid freezing in liquid nitrogen and thawing in ice-cold water. Cell debris and precipitates are removed by high-speed centrifugation and the supernatant is cleared by passage through a 0.45 µm filter. The cleared lysate is diluted to 10 µg/ml in dilution buffer; 20 mM PIPES, 0.15 M NaCl, 0.1% CHAPS, 10%, 5 mM EDTA, 5 mM 2-mercaptoethanol, 2 mM DTT, pH 7.2 and applied to the 96-plate wells. After immobilization for 1 hour at 30° C., the well is washed with the dilution buffer and then incubated with dilution buffer containing 10% nonfat dry milk to block unreacted sites. After the blocking step, the well is washed extensively with the dilution buffer.

Phage expressing displayed antibodies are separated from *E. coli* cells by centrifugation and then precipitated from the supernatant by the addition of 15% w/v PEG 8000, 2.5 M NaCl followed by centrifugation. The purified phage are resuspended in the dilution buffer containing 3% nonfat dry milk and applied to the well containing the immobilized proteins described above, and allowed to bind for 2 hours at 37° C., followed by extensive washing with the binding buffer. Phage are eluted from the well with an elution buffer; 20 mM PIPES, 1 M NaCl, 0.1% CHAPS, 10%, 5 mM EDTA, 5 mM 2-mercaptoethanol, 2 mM DTT, pH 7.2. The well is then extensively washed with purge buffer; 20 mM PIPES, 2.5 M NaCl, 0.1% CHAPS, 10%, 5 mM EDTA, 5 mM 2-mercaptoethanol, 2 mM DTT, pH 7.2. The well is then extensively washed with dilution buffer; 20 mM PIPES, 0.15 M NaCl, 0.1% CHAPS, 10%, 5 mM EDTA, 5 mM 2-mercaptoethanol, 2 mM DTT, pH 7.2. The eluted phage solution is then re-applied to a new well containing adsorbed antigen and the panning enrichment is repeated 4 times. Finally, the phage are eluted from the well with 2M of NaCl in 20 mM PIPES, 0.1% CHAPS, 10%, 5 mM EDTA, 5 mM 2-mercaptoethanol, 2 mM DTT, pH 7.2. Eluates are collected and mixed with log-phase TGl cells, and grown at 37° C. for 1 hour and then plated onto SOB medium containing ampicillin and glucose and allowed to grow for 12-24 hours.

Individual colonies are picked and arrayed into 96-well 2 ml blocks containing SOB medium and M13KO7 helper phage and grown for 8 hours with shaking at 37° C. The phage are separated from cells by centrifugation and precipitated with PEG/NaCl as described above. Concentrated phage are used to infect HB2151 *E. coli*. *E. coli* TGl produces a suppressor tRNA which allows readthrough (suppression) of an amber stop codon located between the scFv and phage gene 3 sequences of the pCANTAB 5 E plasmid. Infected HB2151 cells are selected on medium containing ampicillin, glucose, and nalidixic acid. Cells are grown to mid-log and then centrifuged and resuspended in medium lacking glucose and growth continued. Soluble scFv fragments will accumulate in the cell periplasm. A periplasmic extract is prepared from pelleted cells by mild osmotic shock. The soluble scFv released into the supernatant is purified by affinity binding to Ni-NTA activated agarose and eluted with 10 mM EDTA.

The purified scFv antibody fragments are diluted to 100 µg/ml and applied onto the bioreactive patches with exposed aminoreactive groups using a computer-aided, capillary-based microdispensing system. After an immobilization period of 30 minutes at 30° C., the array is rinsed extensively with 10 mM sodium phosphate, 0.15 M NaCl, 5 mM EDTA, pH 7.0.

Transformed human cells grown in culture are collected by low speed centrifugation, briefly washed with ice-cold PBS, and then resuspended in ice-cold hypotonic buffer containing DNase/RNase (10 g/ml each, final concentration) and mixture of protease inhibitors. Cells are transferred to a microcentrifuge tube, allowed to swell for 5 minutes and lysed by rapid freezing in liquid nitrogen and thawing in ice-cold water. Cell debris and precipitates are removed by high-speed centrifugation and the supernatant is cleared by passage through a 0.45 µm filter. The cleared lysate is applied to the scFv fragment array described above and allowed to incubate for 2 hours at 30° C. After binding, the array is washed extensively with 0.1 M sodium phosphate, 0.15 M NaCl, 5 mM EDTA pH 7.0. The location and amount of bound proteins are determined by optical detection.

Patterns of binding are established empirically by testing dilutions of a control cell extract. Extracts from experimental cells are diluted to a series of concentrations and then tested against the array. Patterns of protein expression in the experimental cell lysates are compared to protein expression patterns in the control samples to identity proteins with unique expression profiles.

Example 7

Formation and use of an Array of Immobilized Monoclonal Antibodies to Detect Concentrations of Soluble Proteins Prepared from Cultured mammalian Cells Collections of monoclonal antibodies are purchased from commercial suppliers as either raw ascities fluid or purified by chromatography over protein A, protein G, or protein L. If from raw ascites fluid, the antibodies are purified using a HiTrap Protein G or HiTrap Protein A column (Pharmacia) as appropriate for the immunoglobulin subclass and species. Prior to chromatography the ascites are diluted with an equal volume of 10 mM sodium phosphate, 0.9% NaCl, pH 7.4 (PBS) and clarified by passage through a 0.22 µm filter. The filtrate is loaded onto the column in PBS and the column is washed with two column volumes of PBS. The antibody is eluted with 100 mM Glycine-HCl, pH 2.7 (for protein G) or 100 mM citric acid, pH 3.0 (for protein A). The eluate is collected into 1/10 volume 1 M Tris-HCl, pH 8.0. The final pH is 7.5. Fractions containing the antibodies are confirmed by SDS-PAGE and then pooled and dialyzed against PBS.

The different samples of purified antibodies are each diluted to 100 µg/ml. Each different antibody sample is applied to a separate patch of an array of aminoreactive monolayer patches (see Example 4, above) using a computer-aided, capillary-based microdispensing system. After an immobilization period of 30 minutes at 30° C., the array is rinsed extensively with 10 mM sodium phosphate, 0.15 M NaCl, 5 mM EDTA, pH 7.0.

Transformed human cells grown in culture are collected by low speed centrifugation, briefly washed with ice-cold PBS, and resuspended in ice-cold hypotonic buffer containing Dnase/Rnase (10 µg/ml each, final concentration) and a mixture of protease inhibitors. Cells are transferred to a microcentrifuge tube, allowed to swell for 5 minutes, and lysed by rapid freezing in liquid nitrogen and thawing in ice-cold water. Cell debris and precipitates are removed by high-speed centrifugation and the supernatant is cleared by passage through a 0.45 µm filter. The cleared lysate is applied to the monoclonal antibody array described above and allowed to incubate for 2 hours at 30° C. After binding the array is washed extensively as in Example 6, above. The location and amount of bound proteins are determined by optical detection.

All documents cited in the above specification are herein incorporated by reference. In addition, the copending U.S. patent application "Arrays of Proteins and Methods of Use Thereof", filed on Jul. 14, 1999, with the identifier 24406-0004 P1, for the inventors Peter Wagner, Dana Ault-Riche, Sleffen Nock, and Christian Itin, is herein incorporated by reference in its entirety. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A molecular array for characterizing molecular interaction events, comprising:
    (a) a substrate; and
    (b) at least one discrete molecular deposition domain on said substrate wherein the spatial address of the domain is less than one micron squared in area and each domain includes a biomolecule deposited on the substrate at a pre-selected location.

2. The molecular array of claim 1 wherein the at least one molecular deposition domain is a spot.

3. The molecular array of claim 1 wherein the at least one molecular deposition domain is an irregular shape.

4. The molecular array of claim 1 wherein the at least one molecular deposition domain is a regular shape.

5. The molecular array of claim 1 wherein the at least one deposition domain is deposited at a known location.

6. The molecular array of claim 1 wherein the molecular deposition domains are affixed to the surface in a high density format.

7. The molecular array of claim 1 wherein the substrate is modified by one or more of the group consisting of gold, an amino group, a carboxyl group, and polymers.

8. The molecular array of claim 1 wherein the substrate is chosen from the group consisting of hydrophobic materials and hydrophilic materials.

9. The molecular array of claim 1 wherein the biomolecule is a protein.

10. The molecular array of claim 1 wherein the biomolecule is an antibody.

11. The molecular array of claim 1 wherein the biomolecule is a nucleic acid.

12. The molecular array of claim 1 wherein the biomolecule is a DNA molecule.

13. The molecular array of claim 1 wherein the biomolecule is an RNA molecule.

14. A molecular array for characterizing molecular interaction events, comprising:
    (a) a substrate; and
    (b) at least one discrete molecular deposition domain on said substrate wherein the spatial address of the domain is less than one micron squared in area and each domain includes a silane deposited on the substrate at a pre-selected location.

15. An array for the identification of a target material comprising:
    a substrate including a substantially flat surface; and
    an at least one discrete deposition domain deposited on said surface, said deposition domain being smaller than one micron squared in total area and deposited at a pre-selected location on the surface, the deposition domain including a long chain biomolecular deposition material having the capacity to bind the target material.

16. The array of claim 15 wherein the deposition material is a protein.

17. The array of claim 15 wherein the deposition material is an antibody.

18. The array of claim 15 wherein the deposition material is a nucleic acid.

19. The array of claim 15 wherein the deposition material is a DNA molecule.

20. The array of claim 15 wherein the surface is chosen from one or more of the group consisting of a hydrophobic surface and a hydrophilic surface.

21. The array of claim 15 wherein the substantially flat surface further comprise a sputter deposited layer of gold thereon, the deposition domain deposited on the gold.

22. An array of deposition domains for the detection of one or more pre-determined target materials comprising:
- a solid glass substrate including a substantially flat surface; and
- an at least one discrete domain deposited on the surface of the substrate, each domain being deposited at a known location and being smaller than one micron squared in area, each domain further including at least one type of molecule with a binding affinity for one or more of the target materials, at least two domains containing different biologically or chemically based molecules.

23. The array of claim 22 wherein the molecule is chosen from one or more of the group consisting of a protein, antibody, nucleic acid, and DNA.

24. The array of claim 22 wherein the surface is modified.

25. A molecular array for characterizing molecular interaction events, comprising:
   (a) a substrate; and
   (b) at least one molecular deposition domain on said substrate wherein the spatial address of the domain is less than one micron squared in area, each domain includes a biologically or chemically based molecule directly deposited on the substrate at a pre-selected location, at least two domains containing different biologically or chemically based molecules.

26. The array of claim 25 wherein the substrate is chosen from one or more of the group consisting of mica, glass, silicon, and quartz.

27. An array, comprising:
   (a) a substrate; and
   (b) at least one patch immobilized on the substrate at a pre-selected location, the at least one patch having an area of about 1 micron squared.

* * * * *